United States Patent
Narendran et al.

(10) Patent No.: US 12,064,507 B2
(45) Date of Patent: *Aug. 20, 2024

(54) COMPOSITION AND METHOD FOR ORAL TREATMENT OF LEUKEMIA

(71) Applicants: Provectus Pharmatech, Inc., Knoxville, TN (US); UTI Limited Partnership, Calgary (CA)

(72) Inventors: Aru Narendran, Calgary (CA); Dominic Rodrigues, Knoxville, TN (US); Bruce Horowitz, Knoxville, TN (US); Edward V. Pershing, Knoxville, TN (US); Eric A. Wachter, Oak Ridge, TN (US)

(73) Assignees: Provectus Pharmatech, Inc., Knoxville, TN (US); UTI Limited Partnership, Calgary (CA)

( * ) Notice: Subject to any disclaimer, the term of this patent is extended or adjusted under 35 U.S.C. 154(b) by 624 days.

This patent is subject to a terminal disclaimer.

(21) Appl. No.: 17/232,393

(22) Filed: Apr. 16, 2021

(65) Prior Publication Data
US 2021/0236418 A1    Aug. 5, 2021

Related U.S. Application Data

(63) Continuation-in-part of application No. 17/214,590, filed on Mar. 26, 2021, and a continuation-in-part of (Continued)

(51) Int. Cl.
*A61K 31/352*  (2006.01)
*A61K 9/00*  (2006.01)
(Continued)

(52) U.S. Cl.
CPC .......... *A61K 9/0019* (2013.01); *A61K 9/0053* (2013.01); *A61K 31/352* (2013.01);
(Continued)

(58) Field of Classification Search
CPC ............ A61K 2300/00; A61K 31/4035; A61K 31/519; A61K 31/522; A61K 31/352;
(Continued)

(56) References Cited

U.S. PATENT DOCUMENTS 5,998,597 A    12/1999  Fisher et al.
6,331,286 B1   12/2001  Dees et al.
(Continued)

FOREIGN PATENT DOCUMENTS

KR    20070022308 A    2/2007
WO      0205812 A1     1/2002
(Continued)

OTHER PUBLICATIONS

Extended European Search Report re application No. EP 21935450.3, dated Nov. 8, 2023.
(Continued)

*Primary Examiner* — Savitha M Rao
(74) *Attorney, Agent, or Firm* — Husch Blackwell LLP

(57) ABSTRACT

A method of treating a mammalian subject having hematologic, non-tumorous cancer cells is disclosed. The method comprises the steps of: (A) administering to such a mammalian subject a therapeutically effective amount of a halogenated xanthene, a pharmaceutically acceptable salt or a C1-C4 alkyl ester thereof as a first cancer cytotoxic agent dissolved or dispersed in a pharmaceutically acceptable aqueous medium. The mammalian subject is maintained for a period of time sufficient to induce death of hematologic, non-tumorous cancer cells. A contemplated administration is typically repeated. A contemplated treatment method can also be carried out in conjunction with administration to said mammalian subject of a second therapeutically effective amount of a second, differently-acting cancer cytotoxic agent dissolved or dispersed in a pharmaceutically accept-
(Continued)

able medium. The second cancer cytotoxic agent can be a small molecule or an intact antibody or paratope-containing portion thereof.

27 Claims, 2 Drawing Sheets

Related U.S. Application Data application No. 16/688,319, filed on Nov. 19, 2019, now Pat. No. 11,419,844.

(60) Provisional application No. 63/000,231, filed on Mar. 26, 2020.

(51) Int. Cl.
*A61K 9/08* (2006.01)
*A61K 9/16* (2006.01)
*A61K 45/06* (2006.01)
*A61P 35/00* (2006.01)
*A61P 35/02* (2006.01)
*C07K 16/28* (2006.01)

(52) U.S. Cl.
CPC ............. *A61K 45/06* (2013.01); *A61P 35/02* (2018.01); *A61K 9/08* (2013.01); *A61K 9/167* (2013.01)

(58) Field of Classification Search
CPC .... A61K 45/06; A61K 9/0019; A61K 9/0053; A61K 9/08; A61K 9/167; A61P 35/00; A61P 35/02; C07K 16/2818; C07K 16/2827; C07K 16/2875
See application file for complete search history.

(56) References Cited

U.S. PATENT DOCUMENTS

| | | | |
|---|---|---|---|
| 6,493,570 | B1 | 12/2002 | Dees et al. |
| 7,390,668 | B2 | 6/2008 | Dees et al. |
| 7,648,695 | B2 | 1/2010 | Dees et al. |
| 8,974,363 | B2 | 3/2015 | Dees et al. |
| 9,107,887 | B2 | 8/2015 | Eagle et al. |
| 9,808,524 | B2 | 11/2017 | Eagle et al. |
| 9,839,688 | B2 | 12/2017 | Eagle et al. |
| 10,130,658 | B2 | 11/2018 | Singer et al. |
| 10,471,144 | B2 | 11/2019 | Eagle et al. |
| 2010/0189651 | A1 | 7/2010 | Stagliano et al. |
| 2015/0126483 | A1 | 5/2015 | Cavanagh et al. |
| 2019/0350893 | A1 | 11/2019 | Singer et al. |
| 2020/0054635 | A1 | 2/2020 | Campbell et al. |

FOREIGN PATENT DOCUMENTS

| | | |
|---|---|---|
| WO | 2005110388 A1 | 11/2005 |
| WO | 2018047917 A1 | 3/2018 |
| WO | 2018191363 A1 | 10/2018 |
| WO | 2019222361 A1 | 11/2019 |

OTHER PUBLICATIONS

Office Action re Japanese application No. JP 2022-562946, dated Dec. 5, 2023.
Saletta, F. et al, "Advances in Paediatric Cancer," Translational Pediatrics, vol. 3, No. 2, pp. 156-182 (2014).
Inaba, H. et al, "Phase I Pharmacokinetic and Pharmacodynamic Study of the Multikinase Inhibitor Sorafenib in Combination with Clofarabine and Cytarabine in Pediatric Relapsed/refractory Leukemia," Journal of Clinical Oncology, vol. 29, No. 4, pp. 3293-3300 (Aug. 20, 2011).
Zwaan, C.M. et al, "Salvage Treatment for Children with Refractory First or Second Relapse of Acute Myeloid Leukaemia with Gemtuzumab Ozogamicin: Results of a Phase II Study," British Journal of Haematology, vol. 48, pp. 768-776 (2010).
Basel, M.T. et al, "Developing a Xenograft Human Tumor Model in Immunocompetent Mice," Cancer Letters, vol. 412, pp. 256-263 (2018).
Yvart, J. et al, "I Rose Bengal: Its use in the Evaluation of Infantile Jaundice," European Journal of Nuclear Medicine, vol. 6, pp. 355-359, (1981).
Wachter, E. et al, "Functional Imaging of Photosensitizers using Multiphoton Microscopy," Multiphoton Microscopy in the Biomedical Sciences II (Ammasi Periasamy and Peter T.C. So, eds.), proceedings of SPIE vol. 4620, pp. 143-147 (2002).
Qin, J. et al, "Colon Cancer Cell Treatment with Rose Bengal Generates a Protective Immune Response via Immunogenic Cell Death," Cell Death and Disease, vol. 8, pp. 1-9 (Feb. 2, 2017). 8:e2584; doi:10.1038/cddis.2016.473.
Toomey, P. et al, "Intralesional Injection of Rose Bengal Induces a Systemic Tumor-Specific Immune Response in Murine Models of Melanoma and Breast Cancer," PLOS ONE, vol. 8, issue 7, (2013); e68561.
Koevary, S.B., "Selective Toxicity of Rose Bengal to Ovarian Cancer Cells in Vitro," International Journal of Physiology, Pathophysiology and Pharmacology, vol. 4, No. 2, pp. 99-107 (2012).
Thompson, J.F. et al, "Chemoablation of Metastatic Melanoma using Intralesional Rose Bengal," Melanoma Research, vol. 18, pp. 405-411 (2008).
Zamani, S. et al, "Rose Bengal Suppresses Gastric Cancer Cell Proliferation via Apoptosis and Inhibits Nitric Oxide Formation in Macrophages," Journal of Immunotoxicology, (2014) (early online: 1-9), DOI:10.3109/1547691X,2013.853715.
Agarwala, S.S, et al, "Phase 1B Study of PV-10 and Anti-PD-1 in Advanced Cutaneous Melanoma," Journal of Clinical Oncology, vol. 37, No. 15, suppl. abstr. 9559 (May 26, 2019).
Swift, L. et al, "Potent in vitro and Xenograft Antitumor Activity of a Novel Agent, PV-10, Against Relapsed and Refractory Neuroblastoma," OncoTargents and Therapy, vol. 12, pp. 1293-1307 (2019).
Thompson, J.F. et al, "Phase 2 Study of Intralesional PV-10 in Refractory Metastatic Melanoma," Annals of Surgical Oncology, vol. 22, No. 7, pp. 2135-2142 (2015).
Foote, M. et al, "Results of a Phase II, Open-Label, Non-Comparative Study of Intralesional PV-10 Followed by Radiotherapy for the Treatment of In-Transit of Metastatic Melanoma," Journal of Surgical Oncology, vol. 115, No. 7, pp. 891-897 (2017).
Liu, H. et al, "Intralesional Rose Bengal in Melanoma Elicits Tumor Immunity via Activation of Dendritic Cells by the Release of High Mobility Group Box 1," OncoTarget, vol. 7, No. 25, pp. 37893-37905, (2016).
Lippey, J. et al, "Intralesional PV-10 for In-Transit Melanoma—A Single Center Experience," Journal of Surgical Oncology, vol. 114, pp. 380-384 (2016).
Ross, M.I., "Intralesional Therapy with PV-10 (Rose Bengal) for In-Transit Melanoma," Journal of Surgical Oncology, vol. 109, No. 4, pp. 314-319 (2014). doi:10.1002/jso.23554.
Liu, H. et al, "T Cell Mediated Immunity after Combination Therapy with Intralesional PV-10 and Blockade of the PD-1/PD-L1 Pathway in a Murine Melanoma Model," PLoS ONE, vol. 13, No. 4, (Apr. 25, 2018); e0196033.
Darvin, P. et al, "Immune Checkpoint Inhibitors: Recent Progress and Potential Biomarkers," Experimental and Molecular Medicine, vol. 50:165 (2018).
Berge, S.M. et al, "Pharmaceutical Salts," Journal of Pharmaceutical Sciences, vol. 66, No. 1, pp. 1-19 (1977).
Fallingborg, J. "Intraluminal pH of the Human Gastrointestinal Tract," Dan Med Bull. Jun. 1999;46(3):183-96. PMID: 10421978. (pubmed.ncbi.nlm.nih.gov/10421978/)—Abstract Only.
Ito, A. et al, "Induction of Thyroid Tumors in (C57BL/6N X C3H/N)F1 Mice by Oral Administration of 9-3',4',5',6'-Tetrachloro-o-carboxy Phenyl-6-hydroxy-2,4,5,7-tetraiodo-3-isoxanthone Sodium (Food Red 105, Rose Bengal B)," JNCI, vol. 77, No. 1, pp. 277-281 (Jul. 1986).

(56) References Cited

OTHER PUBLICATIONS

Batistela, V.R. et al, "pKa Determinations of Xanthene Derivates in Aqueous Solutions by Multivariate Analysis Applied to UV-Vis Spectrophotometric Data," Spectrochimica Acta Part A: Molecular and Biomolecular Spectroscopy, vol. 79, issue 5, pp. 889-897 (Sep. 2011)—Abstract Only.

Hua, S., "Advances in Oral Drug Delivery for Regional Targeting in the Gastrointestinal Tract—Influence of Physiological, Pathophysiological and Pharmaceutical Factors," Frontiers in Pharmacology, vol. 11, article 524, pp. 1-22 (Apr. 2020).

Liu, F. et al, "A Novel Double-Coating Approach for Improved pH-triggered Delivery to the ileo-colonic Region of the Gastrointestinal Tract," European Journal of Pharmaceutics and Biopharmaceutics, vol. 74, pp. 311-315 (2010).

Varum, F.J.O, et al, "A Novel Coating Concept for ileo-colonic Drug Targeting: Proof of Concept in Humans Using Scintigraphy," European Journal of Pharmaceutics and Biopharmaceutics, vol. 84, issue 3, pp. 573-577 (Aug. 2013)—Abstract only.

Hashem, F.M. et al, "In Vitro and In Vivo Evaluation of Combined Time and pH-Dependent Oral Colonic Targeted Prednisolone Microspheres," British Journal of Pharmaceutical Research, vol. 3, No. 3, pp. 420-434 (2013).

Patel, M.M., "Cutting-Edge Technologies in Colon-Targeted Drug Delivery Systems," Expert Opinion Drug Delivery, vol. 8, No. 10, pp. 1247-1258 (2011).

Howard, S.C. et al, "The Tumor Lysis Syndrome," New England Journal of Medicine, vol. 364, No. 19, pp. 1844-1854 (2011). doi: 10.1056/NEJMra0904569.

Akbarzadeh, A et al, "Liposome: Classification, Preparation, and Applications," Nanoscale Research Letters, vol. 8, 102, (2013). https://doi.org/10.1186/1556-276X-8-102.

Dijoseph, J.F. et al, "Antibody-Targeted Chemotherapy with CMC-544: a CD22-Targeted Immunoconjugate of Calicheamicin for the Treatment of B-lymphoid Malignancies," Blood, vol. 103, No. 5, pp. 1807-1814 (Mar. 1, 2004). doi: 10.1182/blood-2003-07-2466.

Francisco, J.A. et al, "cAC10-vcMMAE, an Anti-CD30-monomethyl Auristatin E conjugate with Potent and Selective Antitumor Activity," Blood, vol. 102, No. 4, pp. 1458-1465 (Aug. 15, 2003). doi: 10.1182/blood-2003-01-0039.

Dornan, D. et al, "Therapeutic Potential of an anti-CD79b Antibody-Drug Conjugate, anti-CD79b-vc-MMAE, for the Treatment of Non-Hodgkin Lymphoma," Blood, vol. 114, No. 13, pp. 2721-2729 (Sep. 24, 2009). DOI: 10.1182/blood-2009-02-205500.

Patel, S.P. et al., Poster: Percutaneous Hepatic Injection of Rose Bengal Disodium (PV-10) in Metastatic Uveal Melanoma, American Society of Clinical Oncologists-2020-MUM 20 (May 29-31, 2020).

Shan, C. et al, "Progress of Immune Checkpoint LAG-3 in Immunotherapy," Oncology Letters, vol. 20, 207, (2020). DOI: 10.3892/ol.2020.12070.

Joller, N. et al, "Tim-3, Lag-3, and TIGIT," Curr Top Microbiol Immunol., vol. 410, pp. 127-156 (2017). doi: 10.1007/82_2017_62. PMID: 28900677; PMCID: PMC5902028.

Barretina, J. et al, "The Cancer Cell Line Encyclopedia Enables Predictive Modelling of Anticancer Drug Sensitivity," Nature, vol. 483, pp. 603-607 (2012). https://doi.org/10.1038/nature11003.

Swift, L. et al, "In Vitro Activity and Target Modulation of PV-10 Against Relapsed and Refractory Pediatric Leukemia," Blood, Nov. 29, 2018, vol. 132, supplement 1,: 5207; https://doi.org/10.1182/blood-2018-99-119438.

International Search Report re application No. PCT/US2021/027702, dated Jul. 14, 2021.

Written Opinion re application No. PCT/US2021/027702, dated Jul. 14, 2021.

COMPOSITION AND METHOD FOR ORAL TREATMENT OF LEUKEMIA

CROSS-REFERENCE TO RELATED APPLICATION

This is a continuation-in-part of U.S. patent application Ser. No. 16/688,319, filed on Nov. 19, 2019, and is also a continuation-in-part of U.S. patent application Ser. No. 17/214,590, filed on Mar. 26, 2021, both of whose disclosures are incorporated herein by reference.

FIELD OF THE INVENTION

This invention relates to an oral therapeutic regimen for treating blood (hematologic) cancers such as leukemia particularly effecting such treatments in children.

BACKGROUND ART

An adult human has about 7000 white blood cells per microliter (µL) of blood. Of those white cells, about 65 percent are granulocytes (about 4500/µL), about 30 percent are monocytes (about 2100/µL), and about five percent are lymphocytes (about 350/µL). Geyton, *Textbook of Medical Physiology*, Seventh ed., W. B. Saunders Co., Philadelphia (1986). The above cell number amounts are, of course, generalized average values, and granulocyte counts for normal patients, i.e., patients free of disease, typically are about 2000 to about 7000 cells/µL.

Acute lymphoblastic leukemia (ALL) is a cancer of the lymphoid line of blood cells beginning in the bone marrow, and characterized by the development of large numbers of immature lymphocytes (lymphoblasts). There are two basic types of this disease. One affects B cells (B-ALL), and the other affects T cells (T-ALL). As an acute leukemia, ALL progresses rapidly and is typically fatal within weeks or months if left untreated.

ALL occurs in both children and adults, with highest rates seen between the ages three and seven years. About 75 percent of cases occur before the age of 6, with a secondary rise after the age of 40. The overall incidence of pediatric ALL in the United States during 2001-2014 was 34.0 cases per 1 million persons and among all racial/ethnic groups.

ALL is typically treated initially with chemotherapy aimed at bringing about remission. This is then followed by further chemotherapy typically over three years. Treatment usually also includes intrathecal chemotherapy (spinal cord injection), because systemic chemotherapy can have limited penetration into the central nervous system and the central nervous system is a common site for relapse of ALL.

Chronic lymphocytic leukemia (CLL) is a type of cancer in which the bone marrow makes too many lymphocytes, particularly B cells. Although it is generally considered incurable, CLL progresses slowly in most cases. CLL treatment consequently focuses on controlling the disease and its symptoms rather than on an outright cure. The decision to start CLL treatment is taken when the person's symptoms or blood counts indicate that the disease has progressed to a point where it may affect quality of life.

CLL is primarily a disease of older adults, most commonly occurring in people over the age of 50, with a median age of 70 years at the time of diagnosis. Though less common, CLL sometimes affects people between 30 and 39 years of age. The incidence of CLL increases very quickly with increasing age. Five-year survival following diagnosis is approximately 83% in the United States.

Acute myelogenous leukemia (AML) begins in the bone marrow as a disorder of the hematopoietic stem cell and is the most common form of leukemia in adults. It occurs in both children and adults. Without treatment, AML can rapidly progress in the body as new white blood cells continue being made.

Chronic myelogenous leukemia (CML), also known as chronic granulocytic leukemia (CGL), also starts in the bone marrow, but it progresses less rapidly than AML. In its early phases, CML is characterized by leukocytosis, the presence of increased numbers of immature granulocytes in the peripheral blood, splenomegaly and anemia. These immature granulocytes include basophils, eosinophils, and neutrophils. The immature granulocytes also accumulate in the bone marrow, spleen, liver, and occasionally in other tissues. Patients presenting with this disease characteristically have more than 75,000 white blood cells per microliter (µL), and the count can exceed 500,000/µL.

CML accounts for about 20 percent of all leukemias in the United States. About 15 new cases per million people are reported each year, leading to about 3,000 to 4,000 new cases per year. The disease is rare in humans below age 45, but incidence rises rapidly to age 65, and remains elevated thereafter. The median life span of patients with chronic myelogenous leukemia from the time of diagnosis is approximately four years.

About 60 to 80 percent of patients with CML develop a blast crisis. Blast crisis represents a manifestation of acute leukemia. The presence of certain markers on the blast cells sometimes suggests a lymphoid origin of these cells during the blast crisis.

Chemotherapeutic agents used for the treatment of the blast crisis are the same as those used for the treatment of other acute leukemias. For example, cytarabine and daunorubicin, used for the treatment of acute myelocytic leukemia, are used to treat CML blast crisis. Prednisone and vincristine, a therapeutic regime used in the treatment of acute lymphocytic leukemias, is also used to treat CML blast crisis. Nevertheless, these drug therapies of the blast crisis stage of CML are even less successful than are the treatments of other acute leukemias.

Cancer in children is rare with an incidence of 140-155 per million (age<15 years) per year. This translates to about 1 in 7,000 children is diagnosed with cancer each year. Despite the rarity of cancer, malignant neoplasm is the most common cause of death after accidents in children aged 5 to 14 years, accounting for 23 percent of mortality. Survival from childhood cancers, many of which were fatal in the pre-chemotherapy era, has increased dramatically from 20 to 30 percent in the 1960s to 62 percent in the 1970s, and more recently to 83 percent. Saletta et al., *Transl Pediatr* 3(2): 156-182 (2014).

Leukemias are the most common childhood cancers, accounting for about 30% of all pediatric (ages 1-14) cancer diagnoses. Acute lymphoblastic leukemia (ALL) accounts for about 25 percent of childrens' cancers, and acute myeloid leukemia (AML) accounts for the remaining about 5 percent. Saletta et al., *Transl Pediatr* 3(2):156-182 (2014)

Current treatments for ALL include pegylated asparginase, liposomal daunorubicin, liposomal annamycin, sphingosomal vincristine, and liposomal cytarabine. For AML, current treatments include the use of all-trans-retinoic acid (ATRA), arsenic trioxide, anthracycline combined with ATRA, and idarubicin with high-dose cytarabine. Sorafenib (multikinase inhibitor) in combination with clofarabine and cytarabine has found success in a phase I study [Inaba et al., *J Clin Oncol* 29:3293-3300 (2011)], and a calicheamicin-conjugated CD33 antibody, gemtuzumab ozogamicin, known commercially as Mylotarg®, has shown promise [Zwaan et al., *Br J Haematol* 148:768-776 (2010)].

Although the survival rate for pediatric leukemia has greatly improved, relapse is a major cause of treatment failure. Approximately 15 to 20 percent of pediatric ALL patients and 30 to 40 percent of AML patients relapse, with relapsed ALL identified as the fourth most common malignancy in children.

Treatment of relapsed pediatric leukemia includes intensification of chemotherapeutic regimens and use of bone marrow transplantation (BMT). However, increasing the intensity of combination chemotherapies and introduction of second-line drugs is often accompanied by cumulative toxicity, with marginal incremental benefits.

A key component for understanding immune system interactions against pediatric cancers is the availability of an applicable animal model. Current xenograft models are limited because they are established in severe combined immunodeficient (SCID) mice and so do not provide information on the contribution of the immune system. Other approaches such as human hematopoietic stem cell reconstitution in immunocompetent animals are cumbersome, expensive, and often introduce complex biological variables into the system.

Recently, a novel xenograft tumor model was developed in immunocompetent mice by tolerizing mice fetuses to human tumor cells [Basel et al., *Cancer Lett.* 412:256-263 (2018)]. This model is advantageous because it can be used to better describe the complex interaction between cancerous cells and the immune system through a xenograft technique.

One useful anti-cancer agent group for adult cancerous tumors are the halogenated xanthenes, or the pharmaceutically acceptable salts thereof. See, U.S. Pat. Nos. 6,331,286, 7,390,668, 7,648,695, 9,107,887, 9,808,524, 9,839,688, and 10,130,658. Of those halogenated xanthenes, Rose Bengal disodium, (4,5,6,7-tetrachloro-2',4',5',7'-tetraiodofluorescein disodium; RB) has been found to be particularly effective and easily utilized.

A solution of iodine-131 radiolabeled RB has been used clinically to measure liver function in infants [Yvart et al., *Eur J Nucl Med* 6:355-359 (1981)]. PV-10®, a sterile 10 percent w/v RB disodium solution in aqueous 0.9% sodium chloride for injection is a more recent formulation that is manufactured by Provectus Biopharmaceuticals, Inc. of Knoxville, TN.

Previous studies have shown that RB or its salt from PV-10® aqueous RB disodium solution accumulates in cancerous cell lysosomes [Wachter, et al., *Proceedings of SPIE, Multiphoton Microscopy in the Biomedical Sciences II, Periasamy, A.* and So, P.T.C. (eds), Bellingham, Washington: 4620: 143-147 (2002)] and induces cell death in a range of adult cancers [Qin et al., *Cell Death Dis* 8:e2584 (2017); Toomey et al., *PLoS ONE* 8(7):e68561 (2013); Koevary et al., *Int J Physiol Pathophysiol Pharmacol* 4(2): 99-107 (2012); Thompson et al., *Melanoma Res* 18(6):405-411 (2008); and Zamani et al., *J Immunotoxic* 11(4):367-375 (2014)].

PV-10® aqueous RB disodium solution has been used in several clinical trials, both as a single anti-cancer agent and in conjunction with monoclonal antibody anti-cancer agents, where it has been administered into solid tumor cancers via intralesional (IL) administration. Several of those trials are discussed below. Phase I and phase II clinical studies using PV-10® aqueous RB disodium solution alone as the cytotoxic agent illustratively reported "adverse events were predominantly mild to moderate and locoregional to the treatment site, with no treatment-associated grade 4 or 5 adverse events" [Thompson et al., *Ann Surg Oncol* 22(7): 2135-2142 (2015)], and "Treatment-Emergent Adverse Events (TEAEs) were consistent with established patterns for each drug, principally Grade 1-2 injection site reactions attributed to PV-10® aqueous RB disodium solution and Grade 1-3 immune-mediated reactions attributed to pembrolizumab, with no significant overlap or unexpected toxicities: . . . "[Agarwala et al., *J Clin Oncol* 37(15) suppl 9559-9559 (May 26, 2019)]. It thus appears as though RB is toxic to cancerous cells, but non-toxic to non-cancerous cells.

Because of the often-times very different behavior of adult tumors from pediatric tumors, it was not known whether RB and similar halogenated xanthenes would be effective when used against pediatric cancerous cells and, particularly, pediatric cancerous hematologic cells. Preliminary in vitro and xenograft studies against neuroblastoma cell lines in cell cultures to which RB was added alone or in conjunction with known anticancer agents, and by intralesional injection into solid tumor xenografts established in mice, respectively, were reported by one of the present inventors and co-workers to exhibit killing of pediatric cancerous cells. Swift et al., *Oncotargets Ther,* 12:1293-1307 (February 2019).

In addition, intralesional administration of a halogenated xanthene compound into a tumor provides the active cytotoxic agent directly to the tumor at its highest concentration. In a presently contemplated treatment technique discussed below, administration is often distant from the target cancerous hematologic cells, thereby possibly diminishing the effectiveness of the cancerocidal halogenated xanthene compound medication (agent).

In a phase II clinical trial for patients with refractory metastatic melanoma, intralesional injection of PV-10® aqueous RB disodium solution induced tumor regression with an overall response rate of 51% [Thompson et al., *Ann Surg Oncol* 22(7):2135-2142 (2015)]. Intralesional PV-10® aqueous RB disodium solution also demonstrated efficacy in combination with radiotherapy in a phase II clinical trial for patients with in-transit or metastatic melanoma, with an overall response rate of 86.6% [Foote et al., *J Surg Oncol* 115(7): 891-897 (2017)].

In addition to inducing direct cancer cell death, PV-10® aqueous RB disodium solution intralesional administration has also been shown to induce a tumor-specific immune response in both mouse studies [Qin et al., *Cell Death Dis* 8:e2584 (2017); Toomey et al., *PLoS ONE* 8(7):e68561 (2013); and Liu et al., *Oncotarget* 7(25):37893-37905 (2016)] and in human clinical trials [Lippey et al., *J Surg Oncol* 114(3):380-384 (2016); Ross, *J Surg Oncol* 109(4): 314-319 (2104); Liu et al., *PLoS ONE* 13(4):e0196033 (2018); and Basel et al., *Cancer Lett* 412:256-263 (2018)]. In murine models of melanoma, intralesional treatment with PV-10® aqueous RB disodium solution induced necrosis of melanoma cells and a localized increase in mononuclear tumor-infiltrating lymphocytes [Lippey et al., *J Surg Oncol* 114(3):380-384 (2016)].

It has been suggested that PV-10® aqueous RB disodium solution induced immunogenic cell death, releasing tumor antigens to nearby antigen-presenting cells (APCs), and facilitated the activating of anti-tumor T and B cells. In a syngeneic murine colon cancer model, injection of cancer cells treated in vitro with PV-10® aqueous RB disodium solution into mice with the same tumor resulted in slower tumor growth [Qin et al., *Cell Death Dis* 8:e2584 (2017)].

Furthermore, in syngeneic murine melanoma models, combination treatment with intralesional PV-10® aqueous RB disodium solution and anti-PD-1 antibody delayed tumor growth and enhanced T cell activation [Liu et al., *PLoS ONE* 13(4):e0196033 (2108)].

Parental U.S. application Ser. No. 16/688,319, filed on Nov. 19, 2019, teaches that hematologic cancer cells such as leukemia cells can be successfully treated (killed) by contact with an aqueous composition containing a halogenated xanthene, a pharmaceutically acceptable salt, or a $C_1$-$C_4$ alkyl ester thereof. Co-assigned U.S. application Ser. No. 17/214,590, filed on Mar. 26, 2021, teaches that solid cancerous tumors can be successfully treated by oral administration of a halogenated xanthene, its lactone, or a pharmaceutically acceptable salt or ester thereof. That orally administered medicament could be in solid or liquid form.

The disclosure below describes the contemplated invention and provides results of studies using orally-administered halogenated xanthene compounds such as rose bengal in the treatment of pediatric and adult leukemias.

BRIEF SUMMARY OF THE INVENTION

The present invention contemplates a method of treating a mammalian subject having leukemia. The method comprises the steps of administering to such a mammalian subject a therapeutically effective amount of a halogenated xanthene (HX), a lactone, a pharmaceutically acceptable salt, or a $C_1$-$C_4$ alkyl or aromatic ester thereof (collectively referred to herein as an "HX compound") as a first leukemia cytotoxic agent dissolved or dispersed in a pharmaceutically acceptable diluent solid or liquid medium. A contemplated administration is typically repeated.

A contemplated treatment method can also be carried out in conjunction with administration to that same mammalian subject of a second therapeutically effective amount of a second, differently-acting systemic leukemia cytotoxic agent dissolved or dispersed in a pharmaceutically acceptable medium. The second systemic leukemia cytotoxic agent can be a small molecule, ionizing radiation, or an intact antibody or paratope-containing antibody portion such as those proteinaceous antibody molecules that inhibit inflammatory chemokine activity or immune checkpoint antibodies. The first and the second leukemia cytotoxic agents can be administered together in the same or different medium, or in the same or different medium at different times. The second leukemia cytotoxic agent can be administered in a solid tablet, capsule, pill or the like, in a liquid medium, or as an intravenous injection or infusion.

In one aspect, use of a small-molecule leukemia cytotoxic agent having a molecular weight of about 200 to about 1000 Da is contemplated. Compounds that synergize with a HX Compound such as doxorubicin, etoposide and vincristine are preferred. Intact antibodies or paratope-containing antibody portions are a second group of leukemia cytotoxic agents. Preferred among these agents are those referred to as immune checkpoint inhibitors. [See, for example, Darvin et al., *Exp Mol Med*, 50:165 (2018).]

The present invention also contemplates use of a therapeutically effective amount of an HX compound as a first leukemia cytotoxic agent dissolved or dispersed in a pharmaceutically acceptable aqueous medium for treatment of a mammalian subject having leukemia, wherein the halogenated xanthene compound (HX compound) is maintained in the mammalian subject for a period of time sufficient to induce death of leukemia cells. In a further embodiment, the first leukemia cytotoxic agent HX compound is rose bengal, a pharmaceutically acceptable salt, lactone, or $C_1$-$C_4$ alkyl or aromatic ester thereof. In a still further embodiment, the HX compound is rose bengal disodium salt. Further, the typically treated leukemia cells are acute B-cell or T-cell lymphoblastic leukemia cells, chronic lymphocytic leukemia cells, or acute myeloid leukemia cells.

That any cancer, let alone a solid cancerous tumor of the GI tract like colorectal cancer, could be affected in any way by an orally-administered HX compound as disclosed in U.S. application Ser. No. 17/214,590, filed on Mar. 26, 2021, was quite unexpected because of low HX compound bioavailability, first-pass losses of the drug, and also because of the relatively short circulatory half-time (about 30 minutes) previously reported for HX compounds such as rose bengal (RB) in other contexts. It was thus unexpected that oral administration of rose bengal disodium, an illustrative HX compound, in a pharmaceutically acceptable salt form dissolved in an aqueous diluent, could slow the progress of colorectal tumor development in animals specially bred to develop colorectal tumors in the absence of any treatment. It was even more unexpected that an orally-delivered contemplated HX compound could prevent formation of a colorectal cancerous tumor in those specially bred animals.

That an orally-administered effective amount of an HX compound could also effectively kill leukemia cells, as disclosed herein, was still more unexpected for the reasons discussed above, plus the fact that leukemia cells are distributed through out the body in the blood stream as well as in the bone marrow. Thus, leukemia cells provide lower concentrations of more diffuse targets for the leukemia cytotoxic HX compound to "find" and be taken-up than are the cells of a solid tumor that are relatively more concentrated and directly fed by the tumor's arteries or are contacted by intralesional administration directly into the tumor.

BRIEF DESCRIPTION OF THE FIGURES

In the drawings forming a part of this disclosure.

Figure 1:
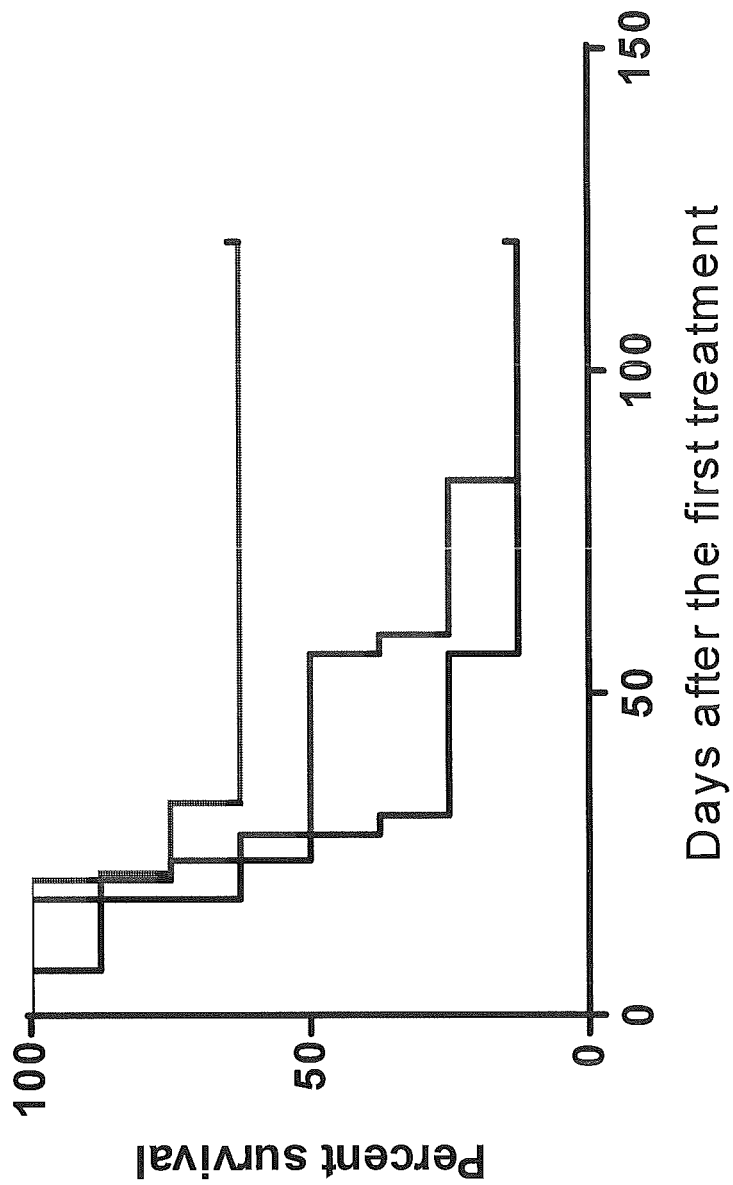
FIG. 1 is a graph showing survival of CB17 SCID mice from Charles River Laboratories International, Inc., treated with orally-administered rose bengal disodium. Exponentially-growing SEM cells ($2.5 \times 10^6$ human ALL cells labelled with GFP) were injected intravenously into each animal and the establishment of tumors was monitored. After 4 weeks to permit the growth of the tumor, mice were randomized to three groups. Group 1 (n=9 control animals) received 100 µL of PBS given orally twice a week for two weeks. Group 2 (n=8 treatment Cohort I animals) received 25 µL of rose bengal disodium present at 10% w/v in 0.9% NaCl aqueous solution that was diluted in PBS to a final volume of 100 µL and given orally twice a week for 2 weeks. Group 3 (n=8 treatment Cohort II animals) received 12.5 µL of the above 10% w/v in 0.9% NaCl aqueous solution that was diluted in PBS to a final volume of 100 µL and administered orally twice a week for 2 weeks. Evidence of disease progression was monitored in all animals and survival was followed up to 120 days following the initiation of treatment. Data are presented as Kaplan-Meier estimates. Examining the region between 50 and 100 days, the line nearest to the X-axis represents data for the controls, the middle line represents data for the Cohort II animals, and the topmost line represents data for the Cohort I animals.

application Ser. No. 17/214,590, filed on Mar. 26, 2021. "Intralesional Administration" represents data present in Thompson et al., Melanoma Res 18:405-411 (2008); "Swift 2018, 2019" are from Swift et al., J Clin Oncol 36:Suppl; abstr 10557 (2018) and Swift et al., Oncotargets Ther 12:1293-1307 (2019); "Oral Apc$^{Min}$" are data from the study reported in U.S. application Ser. No. 17/214,590; and "Oral Leukemia" are new data presented in the present application.

DETAILED DESCRIPTION OF PREFERRED EMBODIMENTS

In one aspect, the present invention contemplates an orally administered pharmaceutical composition for use in treatment (killing) of leukemia cells present in a mammalian subject. A principle cytotoxic agent in that oral pharmaceutical composition is a halogenated xanthene (HX), the lactone thereof, a pharmaceutically acceptable salt thereof, or a $C_1$-$C_4$ alkyl or aromatic ester thereof, that are collectively referred to herein as an "HX compound" that is present in a leukemia-treating effective amount. An orally administered pharmaceutical composition can be in solid or liquid form.

A contemplated halogenated xanthene molecule includes rose bengal (4,5,6,7-tetrachloro-2',4',5',7'-tetraiodofluorescein; RB) that is particularly preferred, erythrosin B, phloxine B, 4,5,6,7-tetrabromo-2',4',5',7'-tetra-iodofluorescein, 2',4,5,6,7-pentachloro-4',5',7'-triiodofluorescein, 4,4',5,6,7-pentachloro-2',5',7'-triiodofluorescein, 2',4,5,6,7,7'-hexachloro-4',5'-diiodofluorescein, 4,4',5,5',6,7-hexachloro-2',7'-diiodofluorescein, 2',4,5,5',6,7-hexachloro-4',7'-diiodofluorescein, 4,5,6,7-tetrachloro-2',4',5'-triiodofluorescein, 4,5,6,7-tetrachloro-2',4',7'-triiodofluorescein, 4,5,6,7-tetrabromo-2',4',5'-triiodofluorescein, and 4,5,6,7-tetrabromo-2',4',7'-triiodofluorescein.

The reader is directed to Berge, J. Pharm. Sci. 1977 66(1):1-19 for lists of commonly used pharmaceutically acceptable acids and bases that form pharmaceutically acceptable salts with pharmaceutical compounds, such as the above halogenated xanthenes. Illustrative cations include alkali metals such as sodium, potassium, as well as ammonium and alkaline earth salts such as magnesium and calcium. The disodium salt of rose bengal is particularly preferred.

The lactone form of a contemplated halogenated xanthene can be formed synthetically and is a preferred precursor of very pure rose bengal. In addition, the carboxylic acid form of a halogenated xanthene salt spontaneously forms the lactone form when in a strongly acidic aqueous environment such as that present in a mammalian stomach. When formed in a mammalian stomach or similarly acidic aqueous medium from the carboxylic acid or carboxylate salt form, the lactone not only forms, but also appears to aggregate into clumps that do not readily dissolve in the duodenum and adjacent small intestinal region or in an aqueous medium having a duodenal pH value.

A $C_1$-$C_4$ alkyl ester of one of the above halogenated xanthene compounds can also be used, with the $C_2$; i.e., ethyl ester, being preferred. In vitro studies using each of RB, ethyl-Red 3 (erythrosine ethyl ester; 2',4',5',7'-tetraiodofluorescein ethyl ester), 4,5,6,7-tetrabromo-2',4',5',7'-tetraiodo-fluorescein, and ethyl-Phloxine B (4,5,6,7-tetrachloro-2',4',5',7'-tetrabromo-fluorescein ethyl ester) exhibit similar anti-tumor activities against CCL-142 renal adenocarcinoma.

A contemplated aromatic ester is formed by a reaction between an HX molecule and an aromatic alcohol having a 5- or 6-membered aromatic ring (including benzyl alcohol), or a 5,6- or 6,6-fused aromatic ring system that contains 0, 1 or 2 hetero ring atoms that are independently nitrogen, oxygen or sulfur. When an aromatic ester is used, it is preferably a benzyl, phenyl, or a 2-, 3-, or 4-pyridyl (pyridyl) ester, other aromatic single and fused ring-containing esters are contemplated as discussed hereinafter. It is to be understood that although a benzyl ester is often considered to be an "aralkyl ester", for the purposes of this invention, a benzyl ester is deemed an aromatic ester.

Illustrative examples of such aromatic alcohol ester portions are shown and named below, where O is an oxygen atom and line-O indicates the ring-oxygen can be from any available carbon of the ring and the O-line crossed by a wavy line indicates that the depicted alkoxy group is a portion of another molecule, the esterified HX molecule.

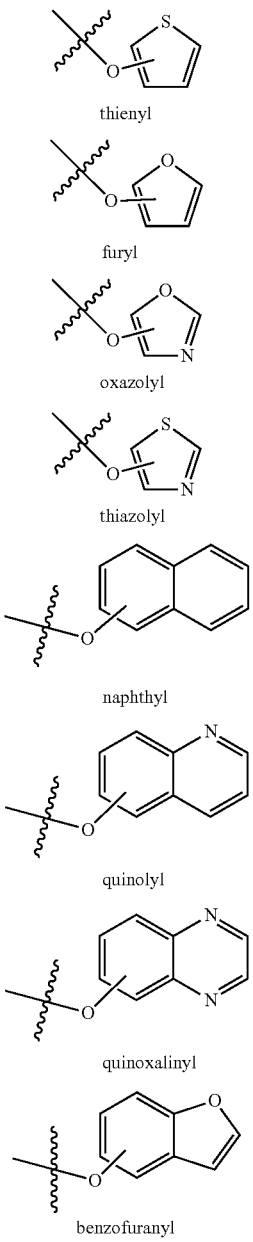

thienyl furyl oxazolyl thiazolyl naphthyl quinolyl quinoxalinyl benzofuranyl

-continued

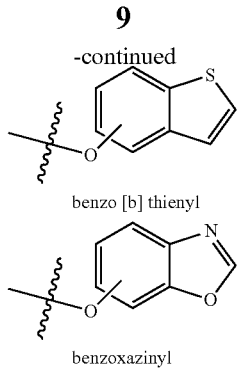

benzo [b] thienyl benzoxazinyl

Rose bengal is a preferred HX molecule and its disodium salt, rose bengal disodium, is a most preferred HX compound. A structural formula of rose bengal disodium is show below:

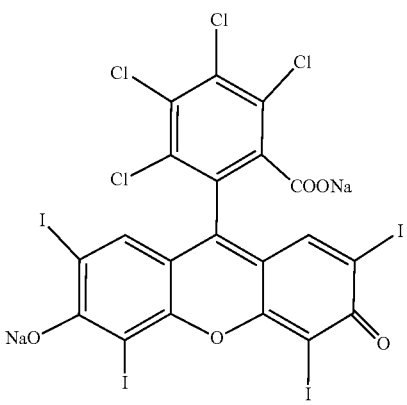

Further details of the medicinal use of a pharmaceutical composition containing an above-noted HX compound are described in U.S. Pat. Nos. 5,998,597, 6,331,286, 6,493,570, 7,390,668, 7,648,695, 8,974,363, 9,107,887, 9,808,524, 9,839,688, 10,130,658 and No. 10,471,144, whose disclosures are incorporated by reference herein in their entireties.
Dosing—FIG. 2

Upon exposure of tumor cells in a 0.9% sodium chloride-containing aqueous medium to an HX compound, irreversible accumulation of the HX compound occurs in tumor lysosomes, causing immunogenic tumor autolysis once a sufficient concentration is achieved to destabilize lysosomal integrity [Wachter et al., *SPIE* 4620:143-147 (2002)]. This suggests that this immunogenic mechanism of cell death can be elicited over a range of exposure conditions based on a (concentration)·(time function), where cytotoxicity is proportional to the product of these two parameters [i.e., cytotoxicity=f([HX]·t), where "t" is time].

For example, when RB is administered in vivo by intralesional injection to a range of solid tumors (e.g., melanoma, hepatocellular carcinoma, breast carcinoma) acute tumor cytotoxicity is evident within approximately 30 minutes for intratumoral RB concentrations of approximately 25-50 mg/g tumor tissue (25-50 mM) [Thompson et al, *Melanoma Res* 18:405-411 (2008)].

Swift et al. [*Oncotargets Ther* 12:1293-1307 (2019)] demonstrated cytotoxicity of treatment-refractory pediatric solid tumors (neuroblastoma and neuroepithelioma) upon in vitro contact with RB for 96 hours at concentrations of approximately 50-100 µM. Additionally, Swift et al., [*J Clin Oncol* 36:Suppl; abstr 10557 (2018)], showed cytotoxicity in additional treatment-refractory pediatric solid tumors (Ewing sarcoma, osteosarcoma and rhabdomyosarcoma) under equivalent exposure.

Extended exposure to RB in the context of continuous oral feeding has been shown to prevent formation of colon cancer (prophylactic activity) and to arrest colon cancer (therapeutic activity) in the murine $Apc^{Min}$ colorectal tumor model as disclosed in parental U.S. application Ser. No. 17/214,590, filed on Mar. 26, 2021. For therapeutic use, symptomatic mice receiving RB ad libitum in drinking water at a concentration of 1 mg/mL had an approximate 38% increase in mean survival relative to untreated mice (12.3±0.5 weeks vs 9.8±0.8 weeks). Presuming a daily drinking water consumption rate of approximately 2 mL/10 g body weight, this corresponds to consumption of approximately 2 mg RB/10 g (200 mg/kg).

Bioavailability of RB disodium administered in aqueous solution via the oral route appears to be limited based on mass balance studies conducted by the inventors, and can be estimated at 0.1-1 percent, corresponding to a daily systemic exposure of 0.2-2 mg/kg. Presuming this amount is distributed through the bloodstream, and that blood volume comprises approximately 10 percent of body weight, this equates to an estimated concentration of 2-20 µM RB in the blood.

This same approach was used to plot data presented in FIG. 1 of the present application, which shows survival of CB17 SCID mice with established xenografts of a pediatric B acute lymphoblastic leukemia (ALL) tumor cell line; therapeutic activity was observed for mice in two treatment groups receiving RB by gavage twice weekly for two consecutive weeks. Assuming 1% bioavailability of this oral RB, an intestinal transit time of 6 hours per administration, and a blood volume of approximately 10 percent of body weight, the two treatment groups correspond to an estimated 125-250 µM RB in the blood.

Figure 2:
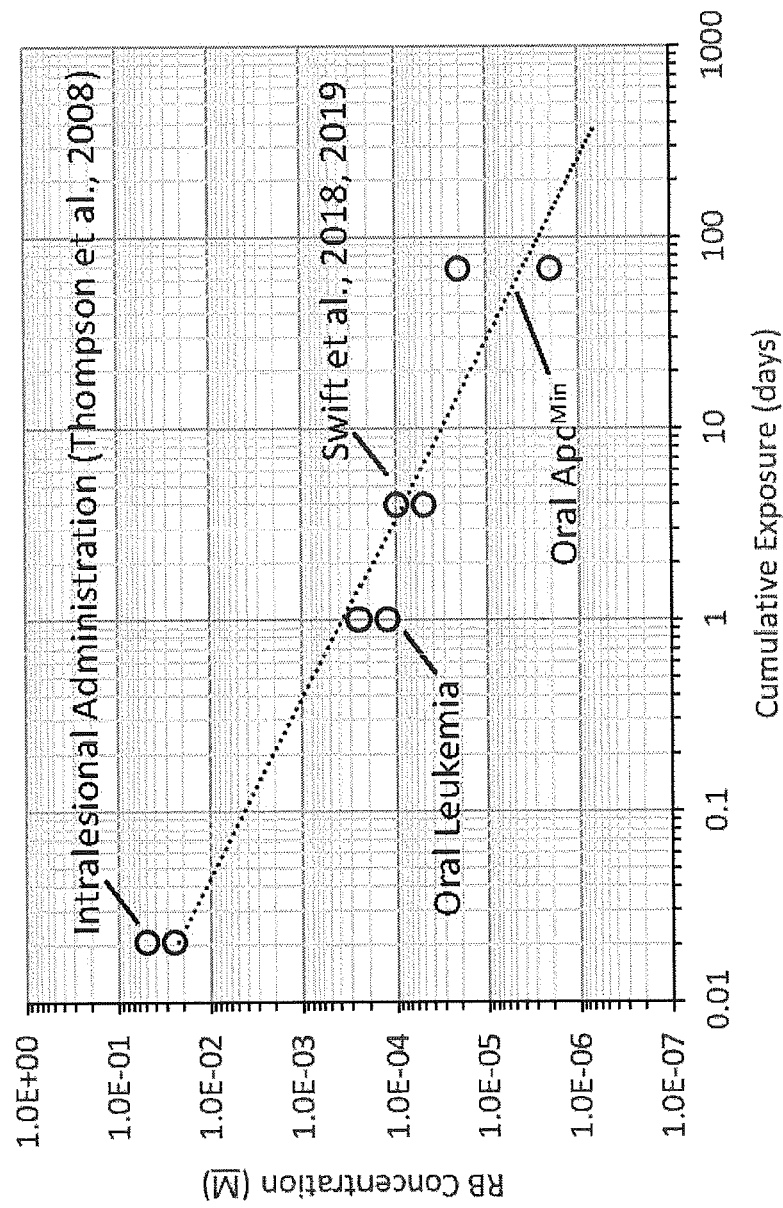
FIG. 2 is a log-log plot of data from several different studies that plots the log of the rose bengal concentration administered (molarity) versus the log of the duration of the HX compound in the subject up to the time of assessing solid tumor treatment, and is also present in an earlier form in U.S.

Plotting these data confirm that the hypothesized relationship (i.e., cytotoxicity=f([HX]·t)) is supported by experimental results, as illustrated in FIG. 2.

More importantly, this functional relationship permits prediction of dose level and schedule appropriate to achieve either an anti-tumor therapeutic outcome upon systemic administration. For extended systemic treatment schedules equivalent to that investigated with the $Apc^{Min}$ model, low micromolar concentrations (i.e., about 10 µM) of circulating HX compound are sufficient to achieve lysosomal accumulation and tumor cell destruction over a period of approximately 3 months, whereas micromolar to submicromolar concentrations (i.e., about 1 µM) are sufficient to achieve tumor cell destruction over a period of approximately 12 months.

Conversely, shorter duration or interrupted repeat systemic dosing at higher dose level, as used in the present oral leukemia model, can also achieve tumor destruction.

For a specific indication, such as treatment of pediatric patients with leukemia, the relationship of FIG. 2 illustrates that standard approaches routinely used by those of skill in the art in pharmaceutical development can be applied to select an appropriate dose level and schedule that maximizes therapeutic outcome while minimizing potential safety risk.

The $Apc^{Min}$ data of application Ser. No. 17/214,590 and the oral leukemia treatment data of the present application show that a simple formulation of the disodium salt of RB is sufficient to deliver a therapeutically active level of RB; however, this may be less than ideally efficient as to bioavailability. Determining a suitable formulation to achieve efficient liberation and absorption of an orally delivered HX compound is thus a matter of standard pharmaceutical development familiar to those of skill in the art, where the properties of the formulation can be varied to achieve desired bioavailability by control of liberation (disintegration, disaggregation and dissolution) at an appropriate point within the GI tract so as to maximize absorption of the dissolved HX compound into the bloodstream.

Formulary optimization can be guided by standard pharmacokinetic study of absorption such that dose level and formulation are adjusted to achieve the necessary systemic exposure on the desired dose schedule (e.g., about 100 µM in the bloodstream for short duration exposure on the order of several days, about 1 to about 10 µM for intermediate duration exposure on the order of several months, to about <1 µM or lower for long-term exposure on the order of a year or more).

The dibasic salt forms of the HX compounds exist in solution having a pH greater than approximately 5, whereas at pH values<5 the HX compounds spontaneously convert to their lactone form. Because the dibasic salt forms are highly soluble in aqueous media, whereas the lactone forms are insoluble in aqueous media, the former exhibit higher bioavailability in the GI tract compared to the latter. Thus, optimizing formulation to properly compensate for the pH value of the GI tract is perhaps the most important parameter affecting bioavailability. For example, in the stomach, where pH value<4, dissolved HX compound is rapidly converted to the insoluble lactone form. Once in the lactone form, the HX compounds exhibit hysteresis and hinderance to saponification back to the absorbable salt form, delaying or inhibiting downstream bioavailability.

However, the intraluminal pH value rapidly increases from highly acidic in the stomach to around pH 6 in the duodenum, and further increases in the small intestine from pH 6 to about pH 7.4 in the terminal ileum; pH drops to 5.7 in the caecum before gradually increasing to pH 6.7 in the rectum. [pubmed.ncbi.nlm.nih.gov/10421978/.] Thus, by applying standard means in the art of pharmaceutical formulation to achieve intestinal liberation, where the favorable pH values facilitate HX compound liberation in a dissolvable, absorbable dibasic salt form, bioavailability is optimized.

For a 12-month treatment regimen, these data indicate that a target concentration of approximately 1 µM (1 mg/L) is achieved in the bloodstream. For a 70 kg adult human, where blood volume comprises approximately 10% of body weight (i.e., about 7 L), this implies absorption of 7 mg HX compound/day. If bioavailability is limited to 1% of administered HX compound, then 700 mg HX compound per os (PO) would be required daily to achieve this target blood level.

However, by optimizing absorption to 50% of administered dose, the necessary PO dose is reduced to approximately 15 mg daily. For a shorter treatment regimen (i.e., 3 months), these data indicate that a target blood concentration of approximately 10 µM (10 mg/L) is achieved. Presuming 1% bioavailability, then 7 g HX compound PO is required daily, whereas at 50% bioavailability, the necessary dose is reduced to approximately 150 mg daily.

One contemplated pharmaceutical composition comprises a 0.1% to about 20% (w/v) aqueous medium (as a liquid) of a first leukemia cytotoxic agent that is a halogenated xanthene compound (HX compound). More preferably, that concentration is about 0.2 to about 10% (w/v), most preferably, the concentration is about 0.2 to about 5% (w/v). Thus, for example, the above dose of 150 mg daily could readily be achieved by use of 3 mL of a 5% (w/v) aqueous solution.

A particularly preferred halogenated xanthene salt is rose bengal (4,5,6,7-tetrachloro-2',4',5',7'-tetraiodofluorescein) disodium (RB disodium) salt. The pharmaceutical composition is administered orally to provide a therapeutically effective amount of a first leukemia cytotoxic agent to a mammal such as a human having leukemia, or more specifically, acute lymphoblastic leukemia (ALL) as T-ALL or B-ALL, chronic lymphocytic leukemia (CLL), or acute myeloid leukemia (AML).

The mammalian subject is typically treated multiple times. The fact and relative amount of leukemia cell killing can be determined by usual means for assaying the status of a given leukemia mammalian subjects. Both the duration of maintenance and the choice to conduct further administrations can depend upon the species of mammal, individual mammalian subjects, the severity of disease, type of disease, age and health of the subject, and the observed effect on the burden of leukemic cells caused by the treatment. These factors are commonly dealt with by physicians skilled in the art of treating leukemia.

In addition, whereas it is typically desired to rid the body of detectable leukemic cells, that cannot always be done. Sometimes it is sufficient to kill enough leukemic cells to control the disease in stasis, or to reduce the leukemic load of cells so that other therapies can be carried out.

The data provided hereinafter illustrate that the $IC_{50}$ value for use of RB against several leukemia cell lines in vitro is about 50 to about 100 µM for exposures of one to several days. Given that the molecular weight of RB disodium is 1018 g/mole, the above $IC_{50}$ value calculates to about 50 to about 100 mg of RB/liter. It is preferred to achieve that concentration for contacting leukemic cells during an in vivo treatment.

The classic intravenous (IV) diagnostic assay for liver function using RB was conducted giving 100 mg RB as a single IV dose. In clinical studies of PV-10® aqueous RB disodium solution, RB has been tolerated at 1500 mg delivered IV. The standard adult blood volume is approximately 5 L. Thus, to achieve 100 mg/L in the blood, an adult patient would need to receive approximately 500 mg of RB IV to achieve the $IC_{50}$ value in the bloodstream. Due to the rapid clearance of RB from circulation ($t_{1/2}$ is about 30 minutes), an IV administration can require continuous infusion to maintain peak levels of RB in circulation (i.e., for up to several hours or more).

Administration at the $IC_{50}$ value level would not be toxic to all circulating hematologic, non-tumorous leukemia cells; i.e., only approximately half of cells would be affected at the $IC_{50}$ value. It can therefore be preferred to administer RB at a multiple of the $IC_{50}$ value, up to approximately 1500 mg (i.e., 300 µM).

Alternatively, it can be sufficient to kill only a fraction of the leukemic cells to initiate a functional immune response against remaining leukemic burden. The latter case can be preferable to avoid toxic reaction (i.e., so-called "tumor lysis syndrome") due to presence of an abundance of rapidly killed leukemia cells. In this situation, the leukemia cell debris caused by the cytotoxicity to leukemia cells of a halogenated xanthene releases intracellular contents such as potassium, causing non-specific cell death. This process may also activate the immune system specifically against the malignant cells.

The similarly useful halogenated xanthene compounds previously-listed and their pharmaceutically acceptable salts can have molecular weights that differ from each other by about a factor of three (See, Table 3, U.S. Pat. No. 7,390,668 at columns 15-16). It is preferred that an exact amount of other than RB halogenated xanthene to be used is calculated based on published molecular weights for each such compound and that of RB or RB disodium.

A mammalian subject having leukemia in need of treatment (a mammalian subject) and to which a pharmaceutical composition containing a halogenated xanthene compound can be administered can be a primate such as a human, an ape such as a chimpanzee or gorilla, a monkey such as a cynomolgus monkey or a macaque, a laboratory animal such as a rat, mouse or rabbit, a companion animal such as a dog, cat, horse, or a food animal such as a cow or steer, sheep, lamb, pig, goat, llama or the like.

In one aspect of the invention, a contemplated HX compound for oral administration is typically used dissolved or dispersed in a sterile aqueous pharmaceutical composition. Sterile tap water or sterile water from another source can be used.

Characteristics of a Contemplated Liquid Pharmaceutical Composition

An HX compound is typically present in a contemplated aqueous pharmaceutical composition at about 0.1 to about 20% (w/v). More preferably, that concentration is about 0.2 to about 10% (w/v), most preferably, the concentration is about 0.2 to about 5% (w/v). Thus, for example, the above dose of 150 mg daily could readily be achieved by use of 3 mL of a 5% (w/v) aqueous solution.

The bioavailability of various HX compounds such as disodium rose bengal has not been well characterized. Studies commissioned by one of the assignees concluded that bioavailability of disodium rose bengal is less than (<) 1% based on radiolabel studies where $^{14}$C-RB in aqueous solution was given orally to mice. In the stomach, with a pH value<4, an HX compound is likely to be in the lactone form. Conversion to lactone in the stomach does not destroy the HX compound, but such conversion into the lactone form can present a kinetic and/or thermodynamic barrier to reconversion to the soluble salt form necessary for absorption in the intestines.

The study discussed in U.S. patent application Ser. No. 17/214,590 using Apc$^{min}$ mice showed that those mice consumed 4 mg/mL ad libitum in drinking water arrested onset of disease. Those Apc$^{min}$ mice are understood to have thereby consumed approximately 8 mg/10 g/day=800 mg/kg/day. That amount is consistent with toxicology data showing such a dose is tolerated. Thus, Ito et al., *J Natl Cancer I*, 77:277-281 (1986) studying rose bengal as a food coloring (Food Red No. 105) found that rose bengal fed ad libitum continuously for 2 years at a dose of 970 mg/kg/day to C57BL6N mice was well tolerated. The previously used intravenous (IV) liver diagnostic delivered 112 mg of rose bengal as a bolus; for a standard 60 kg adult human, which equates to 1.9 mg/kg; this has not reported to yield morbidity.

It is preferred that a liquid pharmaceutical composition for oral administration have an osmolality less than that of blood plasma. Normal (well) human reference range of osmolality in plasma is about 275-299 milli-osmoles per kilogram (mOsm/kg).

More preferably, that composition is free of tonicity agents (or tonicity-adjusting agents) such as sugars like mannitol and dextrose, $C_3$-$C_6$ polyhydroxy compounds such as propylene glycol, glycerol and sorbitol, isotonic salts such as sodium or potassium chloride, and/or buffering agents other than those such as citric acid, malic acid, acetic acid and other food acids and their salts that can be provided for flavor and mild buffering (less than 5 mmol of buffering agent). The stomach and lower GI tract are well adapted to provide the proper tonicity to materials flowing through such that further salts and/or buffers are not needed. One or more pharmaceutically acceptable taste-masking agents or flavorants as are well-known can be present at up to about 5% by weight to enhance the potability of the composition.

It is preferred that the pH value of a pharmaceutically acceptable aqueous diluent be about 5 to about 9, to yield maximum solubility of the HX compound in an aqueous vehicle and assure compatibility with biological tissue. A particularly preferred pH value is about 5 to about 8, and more preferably between about 6 to about 7.5. At these pH values, the halogenated xanthenes typically remain in dibasic form, rather than the lactone that forms at low pH values.

An HX compound such as rose bengal is dibasic, having pKa values of 2.52 and 1.81. pKa value determinations for several contemplated halogenated xanthenes can be found in Batistela et al., *Spectrochim Acta Part A* 79(5):889-897 (September 2011).

In the present invention, the specific amount of halogenated xanthene compound in a pharmaceutical composition is not believed to be as important as was the case where the composition was injected intralesionally to a tumor because the object here is to ultimately provide a cytotoxic concentration of halogenated xanthene compound to the environment of the leukemic cells and in which those leukemic cells can be contacted with the halogenated xanthene compound. The data provided hereinafter indicate that an IC$_{50}$ concentration of disodium rose bengal is about 50 to about 100 µM for in vitro cultured leukemia cells.

The above-noted results using in vitro cultured leukemia cells surprisingly provided data similar to those obtained in an in vitro cytotoxicity study of cultured SK-N-AS, SK-N-BE(2), IMR5, LAN1, SHEP, and SK-N-SH neuroblastoma cells, SK-N-MC neuroepithelioma cells, and normal primary, BJ, and WI38 fibroblasts reported by Swift et al., *OncoTargets and Therapy* 12:1-15 (2019). Those authors reported half maximal inhibitory concentration (IC$_{50}$) values for PV-10® aqueous RB disodium solution-treated cells at 96 hours post treatment of 65-85 µM for the neuroblastoma lines assayed and 49 µM for the neuroepithelioma line SK-N-MC. Those authors also examined toxicity toward human epithelial cells from three tissue sources and reported IC$_{50}$ values of 93-143 µM.

In clinical studies of PV-10® aqueous RB disodium solution, RB has been tolerated at 1500 mg delivered IL. Due to the rapid clearance of RB from circulation (t$_{1/2}$ about 30 minutes) an IV administration can require continuous infusion to maintain peak levels of RB in circulation (i.e., for up to several hours or more) during a single administration.

Characteristics of a Contemplated Solid Pharmaceutical Composition

It is further contemplated that the HX compound such as RB or disodium RB, or a HX compound lactone such as RB lactone be administered in a solid pharmaceutical composition for oral administration that is enterically-coated to pass through the stomach and release the HX compound in the intestines. The HX compound is typically dissolved in or dispersed in or on a solid diluent medium.

There are several factors at play in the dissolution of an orally administered solid pharmaceutical product in a mammalian body. Among those factors are residence time of the medicament at different locations along the GI tract, particle size, solubility of the individual components of the medicament in the bodily fluids likely to be encountered from mouth to anus, the order in which various coating layers, when present, are applied to the medicament, as well as the pH value at which a particular coating layer is soluble.

For example, the highly acidic gastric environment (pH 1.5-2 in the fasted state; pH 3-6 in the fed state) rises rapidly to about pH 6 in the duodenum and increases along the small intestine to pH 7.4 at the terminal ileum. The pH value in the cecum drops just below pH 6 and again rises in the colon reaching pH 6.7 at the rectum [Hua, *Front Pharmacol* 11:Article 524 (April 2020)]. Observation of solutions of disodium RB mixed into a water solution having the pH value of the human stomach revealed rapid clouding of the admixture and clumping of the previously soluble disodium RB, presumably into the lactone form.

Gastric transit can range from 0 to 2 hours in the fasted state and can be prolonged up to 6 hours in the fed state. In general, the transit time in the small intestine is considered relatively constant at around 3 to 4 hours, but can range from 2 to 6 hours in healthy individuals. Colonic transit times can be highly variable, with ranges from 6 to 70 hours reported [Hua, *Front Pharmacol* 11:Article 524 (April 2020)].

Drugs must pass or permeate through the epithelial cells that line the inner walls of the GI tract in order to be absorbed into the circulatory system. A cellular barrier that can prevent epithelial cell absorption of a given drug is the cell membrane. Cell membranes are essentially lipid bilayers that form a semipermeable membrane.

Pure lipid bilayers are generally permeable only to small, uncharged solutes. Hence, whether or not a molecule is ionized will affect its absorption, because ionic molecules are charged. Solubility favors charged species, and permeability favors neutral species.

Typically, ions cannot passively diffuse through the gastrointestinal tract because the epithelial cell membrane is made up of a phospholipid bilayer. The bilayer is made up of two layers of phospholipids in which the charged hydrophilic heads face outwards and the non-charged hydrophobic fatty acid chains are in the middle of the layer. The uncharged fatty acid chains repel ionized, charged molecules. This means that the ionized molecules cannot easily pass through the intestinal membrane and be absorbed.

Chemical modification by esterification can be used to control solubility. For example, $C_2$-$C_4$ alkyl and aromatic ester forms of an HX compound typically have decreased solubility in aqueous liquids, and because of their neutral ionic charge, are typically better taken-up by intestinal epithelial cells than their carboxylate forms. Later, esterases in the GI tract wall and blood hydrolyze these esters to release the parent drug.

Also, coating films on a tablet or a pellet can act as a barrier to reduce the rate of dissolution and/or disintegration of the composition in aqueous media, generally, and particularly within the stomach. A coating can also be used to modify where dissolution takes place. For example, enteric coatings can be applied to a drug-containing medicament, so that the coating and the drug only dissolve in the basic environment of the intestines. One approach useful for predictable release of a drug from a medicament in the intestinal portion of the GI tract and/or at a particular location in the GI tract relies upon pH-specific coatings and matrices that dissolve or disintegrate at preselected GI tract pH values such as those noted previously.

The table below shows some examples of pH-dependent polymer coatings that have been used for the purpose of targeting release (local treatment) either alone or in combination, including some methacrylic resins (commercially available from Evonik Industries, AG, Essen, Germany as Eudragit®), and hydroxypropyl methylcellulose (HPMC; available from DuPont, Wilmington, DE as Methocel™; and Ashland, Inc., as Benecel™, Wilmington, DE) derivatives. In addition to triggering release at a specific pH value range, the enteric coating can protect the incorporated active agent against the harsh GI tract environment (e.g., gastric juice, bile acid, and microbial degradation) and can create an extended and delayed drug release profile to enhance therapeutic efficiency.

The "published pH release" value for each polymer is from the manufacturer. The "published pH release" values are not absolute for all compositions or environments, and pH values for dissolution or disintegration stated herein are based on those published values.

| pH-Depending Polymer Coatings* | |
| --- | --- |
| Polymer | Published pH Release |
| Eudragit ® S-100 | 7.0 |
| Eudragit ® FS-30D | 7.0 |
| Eudragit ® L-100 | 6.0 |
| Cellulose acetate phthalate | 6.0 |
| Cellulose acetate trimellitate | 5.5 |
| Eudragit ® L-30D-55 | 5.5 |
| Eudragit ® L-100-55 | 5.5 |
| Hydroxypropyl methylcellulose phthalate 55 | 5.5 |
| Hydroxypropyl methylcellulose phthalate 50 | 5.0 |
| Polyvilyl acetate phthalate | 5.0 |

*[Hua, Front Pharmacol 11:article 524 (April 2020)]

For colonic release, colon-targeted drug delivery systems have been actively pursued because conventional non-targeted therapy can have undesirable side-effects and low efficacy due to the systemic absorption of drug before reaching the target site. Liu et al., *Eur. J. Pharm. Biopharm.* 74:311-315 (2010), adopted dual coating approach by using the alkaline aqueous solution of Eudragit® S with buffering agents for inner layer and the organic solution of Eudragit® S for outer layer, accelerating the drug dissolution at pH values greater than 7. Subsequently, Varum et al., *Eur. J. Pharm. Biopharm.* 84:573-577(2013), evaluated in vivo performance of this dual coated system in humans, demonstrating more consistent disintegration of dual coated tablets mainly in the lower intestinal tract.

Hashem et al., *Br. J. Pharm. Res.* 3:420-434 (2013), developed microspheres combining time- and pH-dependent systems for colonic delivery of prednisolone. By using a combination of Eudragit® S and ethyl cellulose, they achieved greater colonic drug delivery, while preventing premature drug release in the upper intestine.

Eudracol® is another example of a multi-unit technology providing targeted drug delivery to the colon, with delayed and uniform drug release. This system is based on coating the pellet with Eudragit® RL/RS and Eudragit® FS 30D, providing colon-specific drug release in a pH- and time-dependent manner [Patel, *Expert Opin. Drug Deliv.* 8:1247-1258 (2011)].

One composition that targets the small intestine comprises a diluent medium of sugar/sucrose beads coated with particulate rose bengal (RB) that is coated with one or a plurality of layers of a (meth)acrylate copolymer that is composed of about 60 to about 95% by weight free radical polymerized $C_1$-$C_4$-alkyl esters of acrylic or methacrylic acid and about 5 to about 40% by weight (meth)acrylate monomers with an acidic group in the alkyl radical.

Particularly suitable (meth)acrylate copolymers include about 10 to about 30% by weight methyl methacrylate, about 50 to about 70% by weight methyl acrylate and about 5 to about 15% by weight methacrylic acid (Eudragit® FS type). Similarly suitable, are (meth)acrylate copolymers of about 20 to about 40% by weight methacrylic acid and about 80 to about 60% by weight methyl methacrylate (Eudragit® S type). The word "(meth)acrylate" is used herein to mean that either or both of acrylate and methacrylate monomers can be used.

These coating polymers permit little if any HX compound release prior to the particles leaving the stomach. The pH value of the fluid within the duodenum typically is about 6 and rises to about 7.4 toward the ileum.

A usual tablet or lozenge can be prepared by admixture of lactose (20%) and active ingredient (80%; HX compound) mixed in a high-speed mixer (DIOSNA type P10, Osnabruck, Germany). An aqueous solution containing the excipient polyvinylpyrrolidone (PVP) such as povidone (Sigma-Aldrich International GmbH, Buchs, CH) is added in small amounts until a homogeneous composition is obtained. The moist powder mixture is screened. Tablets are subsequently made therefrom as is well-known, and dried.

The resulting tablets or lozenges are thereafter preferably coated with a protective polymer film, often using fluidized bed equipment. Film-forming polymers are normally mixed with plasticizers and release agents by well-known processes. The film formers can in this case be in the form of a solution or suspension. The excipients for the film formation can likewise be dissolved or suspended. Organic or aqueous solvents or dispersants can be used. Stabilizers can be used in addition to stabilize the dispersion (for example: Tween® 80 or other suitable emulsifiers or stabilizers).

Examples of release agents are glycerol monostearate or other suitable fatty acid derivatives, silicic acid derivatives or talc. Examples of plasticizers include propylene glycol, phthalates, polyethylene glycols, sebacates or citrates, and other substances mentioned above and in the literature.

Another preferred type of medicament is a water-soluble capsule or blister that contains a plurality of particles of an HX compound such as rose bengal disodium or rose bengal lactone that are covered with one or more layers of polymeric resin that release the HX compound quickly upon dissolution or disintegration of the capsule in water or body fluid. Capsules are typically made of gelatin and are often referred to as gelcaps. Gelatin is an animal product. Vegetarian capsules are often made of hydroxypropyl methyl cellulose (HPMC).

In some embodiments, the HX compound is directly layered with one or more coats of the polymer to form particles that are generally spherical in shape. Such particles are often referred to as beads. In a preferred aspect, particles (beads) are sized so as that about 90 percent by weight pass through a 20 mesh sieve (opening=850 µm) screen and about 90 percent by weight are retained on an 80 mesh sieve (opening=180 µm) screen.

Exemplary pH value-sensitive coating polymeric resins are discussed above. The pH value-sensitivity of coating polymeric resins is to be understood in terms of physiologically present pH values along the GI tract such as those discussed above.

In other embodiments, small pellets such as sugar/starch seeds, non-pareils or prills, which are small, generally spherically-shaped cores, are coated with a plurality of layers of the HX compound and one or more layers of polymeric coating. Illustrative sugar/starch cores are sugar spheres NF that pass through an about 40 mesh sieve (425 mm opening) screen to an about 50 mesh sieve (300 mm opening) screen, that contain not less than 62.5 percent and not more than 91.5 percent sucrose, calculated on the dry basis, the remainder consisting primarily of starch. (USP NF 1995 2313).

In an illustrative example, a 100 kilogram (kg) quantity of disodium rose bengal, a 7.1 kg quantity of cross-linked carboxymethyl cellulose (preferably croscarmellose sodium NF), and an 11.9 kg quantity of starch NF, are each divided in half, and the three constituents are blended together to form two identical batches. Each of the batches is milled through an 80 mesh screen using a mill such as a Fitzpatrick Mill. The two milled batches are then blended to form a mixture, which is tested for composition in accordance with accepted quality assurance testing methods that are well-known by those skilled in the art.

The disodium rose bengal mixture is subsequently divided into three equal parts, with a first part remaining whole, and second and third parts each divided into lots of 50 percent, 30 percent and 20 percent. A 25.6 kg quantity of 40-50 mesh sugar/starch seeds (e.g., sugar spheres NF) is placed in a stainless steel coating pan. An 80 liter (L) quantity of 5 percent povidone/iso-propanol (IPA) solution is prepared for spraying onto the particles.

The coating pan is started with the sugar spheres, onto which is sprayed an application (approximately 0.173 kg per application) of the povidone-alcohol solution, and onto which is sifted an application (approximately 0.32 kg) of the disodium rose bengal mixture from the first part (that part that remained whole). Sifting is done using a standard sifter. The spraying and sifting steps are continued until the first part of the mixture has been applied to the sugar spheres to form a batch of partially coated spheres.

The partially coated spheres are then divided into two equal lots, each lot being placed in a coating pan. Separately for each of the two lots, spraying of the povidone/IPA solution and sifting of the disodium rose bengal mixture as divided into the 50 percent lots continues until the 50 percent lots have been applied to the spheres. Following application of the 50 percent lots, the spheres can be screened using a 25 mesh screen if necessary.

The spraying of the povidone/IPA solution and sifting of the disodium rose bengal mixture as divided into the 30 percent lots commences and continues until the 30 percent lots have been applied to the spheres. The coated spheres can be rescreened using a 25 mesh screen.

Spraying of the povidone/IPA solution and sifting of the disodium rose bengal mixture continues using the mixture as divided into the 20 percent lots until the 20 percent lots have been applied to the spheres. At this point in the process, the entire quantity of the disodium rose bengal mixture has been applied to the spheres, and about 50 kg of the 5 percent povidone/IPA solution has been applied to the spheres.

A 7.5 percent povidone/IPA solution is prepared and applied to the spheres as a sealant. The sealed spheres are tumble dried for about one hour, weighed, and placed in an oven at about 122° F. (50° C.) for 24 hours. After drying, the spheres are screened through a 20 mesh screen and a 38 mesh screen to form the immediate (quick or fast as compared to delayed) release particles.

The above-discussed HX compound-containing spheres or their capsule (or blister) can also be coated with a pH value-sensitive enteric coating polymer as discussed previously so that once released in the GI tract, the spheres do not provide their active ingredient, HX compound, to their surroundings unless the pH value is at least that of a desired GI tract location.

Another way to control the location of HX compound release is to further coat the spheres (HX-coated particles) discussed above, with a dissolution-controlling coat of polymeric resin applied to the surface of the spheres such that the release of the HX compound from the spheres is controlled and released over a 6-10 hour period. The materials used for this purpose can be, but are not limited to, ethylcellulose, hydroxypropylmethyl-cellulose, hydroxypropylcellulose, methylcellulose, hydroxyethylcellulose, nitrocellulose, carboxymethyl-cellulose, as well as copolymers of ethacrylic acid and methacrylic acid (Eudragit®), or any other acrylic acid derivative (Carbopol®, etc.) can be used.

In addition, an enteric coating material can also be employed, either singularly, or in combination to the above non-pH-sensitive coatings. These materials include, but are not limited to, hydroxypropylmethylcellulose phthalate and the phthalate esters of all the cellulose ethers. In addition, phthalate esters of the acrylic acid derivatives (Eudragit®), or cellulose acetate phthalate.

These coating materials can be employed in coating the surfaces in an amount of about 1.0 percent (w/w) to about 25% (w/w). Preferably, these coating materials are present at about 8.0 to about 12.0 percent (w/w).

Excipients

Excipients customary in pharmacy can be employed in a manner known per se in the production of the HX compound-containing medicament. These excipients can be present in the core or in the coating agent.

Polymers

Polymeric materials used as adhesives in helping to adhere an HX compound to a sugar prill or sphere is deemed to be an excipient where coating layers of an HX compound are employed. Illustrative of such polymers are polyvinyl pyrrolidone and polyvinyl alcohol as are other water-soluble, pharmaceutically acceptable film-forming polymers such as hydroxypropyl cellulose.

Dryers (Non-Stick Agents)

Dryers have the following properties: they have large specific surface areas, are chemically inert, are free-flowing and comprise fine particles. Because of these properties, they reduce the tack of polymers containing polar comonomers as functional groups. Examples of dryers are: alumina, magnesium oxide, kaolin, talc, fumed silica, barium sulphate and cellulose.

Disintegrants

Disintegrants are added to oral solid dosage forms to aid in their disaggregation. Disintegrant are formulated to cause a rapid break-up of solids dosage forms on contacting moisture. Disintegration is typically viewed as the first step in the dissolution process. Illustrative disintegrants include sodium croscarmellose, an internally cross-linked sodium carboxymethyl cellulose, cross-linked polyvinylpyrrolidone (crospovidone) and sodium starch glycolate.

Release Agents Examples of release agents are: esters of fatty acids or fatty amides, aliphatic, long-chain carboxylic acids, fatty alcohols and their esters, montan waxes or paraffin waxes and metal soaps; particular mention should be made of glycerol monostearate, stearyl alcohol, glycerol behenic acid ester, cetyl alcohol, palmitic acid, carnauba wax, beeswax, and the like. The usual proportionate amounts are in the range from 0.05 percent by weight to 5, preferably 0.1 to 3 percent by weight based on the copolymer.

Other Excipients Customary in Pharmacy

Mention should be made here of, for example, stabilizers, colorants, antioxidants, wetting agents, pigments, gloss agents. They are typically used as processing aids and are intended to ensure a reliable and reproducible production process and good long-term storage stability. Further excipients customary in pharmacy may be present in amounts from 0.001% by weight to 10% by weight, preferably 0.1 to 10% by weight, based on the polymer coating.

Plasticizers

Substances suitable as plasticizers ordinarily have a molecular weight between 100 and 20,000 and comprise one or more hydrophilic groups in the molecule, e.g. hydroxyl, ester or amino groups. Citrates, phthalates, sebacates, castor oil are suitable. Examples of further suitable plasticizers are alkyl citrates, glycerol esters, alkyl phthalates, alkyl sebacates, sucrose esters, sorbitan esters, dibutyl sebacate and polyethylene glycols 4000 to 20 000. Preferred plasticizers are tributyl citrate, triethyl citrate, acetyl triethyl citrate, dibutyl sebacate and diethyl sebacate. The amounts used are between 1 and 35, preferably 2 to 10, % by weight, based on the (meth)acrylate copolymer.

Optimizing Systemic Bioavailability

The amount of HX compound delivered by a solid medicament composition is substantially the same as that from an aqueous composition. Administration of sufficient RB, as an illustrative HX compound, to achieve a circulating RB concentration at the $IC_{50}$ level would not by definition be toxic to all circulating leukemic cells (i.e., only approximately half of the leukemic cells would be affected at the $IC_{50}$). In some embodiments it can be preferred to administer RB in an amount that is a multiple of the $IC_{50}$ level, up to approximately 1500 mg (i.e., 300 mM). Alternatively, however, it can be sufficient to kill only a fraction of tumor cells as a result of an individual administration.

The latter case can be preferable for avoiding a toxic reaction (i.e., "tumor lysis syndrome") that can result from rapidly killed tumor cell burden. Thus, Howard et al., *N Engl J Med* 364(19):1844-1854 (May 12, 2011) report that tumor lysis syndrome is the most common disease-related emergency encountered by physicians treating hematologic cancers such as leukemia.

As discussed in greater detail below, it can also be advantageous to kill only a portion of the leukemic cells during a single treatment to initiate a functional immune response against remaining leukemia cell burden. A RB-initiated functional immune system response is believed to occur due at least in part from the action of RB-caused necrotic cell debris circulating in the body induces an immune response that can prolong the effects of an initial administration of a halogenated xanthene such as RB.

An induced immune response can take a longer time to develop than the more immediate killing of the contacted leukemic cells. That delay in effect can occur because of the time needed for induction the appropriate B and T cell populations to attack and kill the leukemic cells as well as to induce long lasting memory T cells whose continued circulation can protect the patient from relapse. Such an initial delay can be augmented for the subject's life-time due to the memory immune cells so induced.

Combination Treatment

In another aspect, an above pharmaceutical composition is used in conjunction with a second, differently-acting systemic cytotoxic anti-leukemia agent; i.e., a cytotoxic anti-leukemia agent whose mechanism of action is different from that of the first cytotoxic agent, the HX compound. As noted previously, the halogenated xanthenes localize in cancer cell lysosomes, increase the percentage of cells in G1 phase of the cell cycle and induces cell death by apoptosis [Swift et al., *Oncotargets Ther,* 12:1293-1307 (February 2019)].

A first type of second anti-leukemia systemic cytotoxic agent is a so-called "small molecule." Such small molecules can be viewed as semi-specific cellular poisons in that they are only generally more specific at killing leukemia cells than non-leukemic cells. Almost all small molecule anticancer agents are less leukemia-specific than a contemplated HX compound, and can result in causing sickness, baldness and other trauma to their recipient subjects that can lead to subjects leaving their treatment regimens.

These small molecules typically have molecular weights of about 150 to about 1000 Daltons (Da), and preferably about 250 to about 850 Da. This group of small molecules includes many of those used to treating hematologic leukemias such as calicheamicin (1368 Da), vinblastine (811 Da), vincristine (825 Da), imatinib (494 Da), monomethyl auristatin (718 Da), etoposide (589 Da), daunorubicin (528 Da), doxorubicin (544 Da), cladribine (286 Da), fludarabine (365 Da), mitoxantrone (444 Da), 6-thioguanine (167 Da), methotrexate (454 Da), 6-mercaptopurine (152 Da), azacytidine (244 Da), annamycin (640 Da), sorafenib (465 Da), clofarabine (304 Da), cisplatin (300 Da), irinotecan (587 Da) and cytarabine (243 Da). One or more of the above small molecule anti-leukemia can comprise a second leukemia cytotoxic agent. It is noted that many of these small molecules are used as their salts, prodrugs and/or esters, which consequently have greater molecular weights than those rounded values above.

A pharmaceutical composition having a second systemic cytotoxic anti-leukemia agent can also contain a small molecule as above-described that is conjugated to a lager molecule such as a protein, detergent and/or polymer such as poly(ethylene glycol) [PEG]. Such conjugations often minimize the toxicity of the small molecule and enhance situs of delivery as use of an antibody that binds to a leukemic cell. Additionally, a small molecule cytotoxic agent can be enveloped within a liposome, micelle or cyclodextrin molecule that can be adapted to bind specifically bind to leukemic cells and/or be endocytosed by the leukemia cell. This group of encapsulated and conjugated small molecules is included with the previously discussed small molecule group of second systemic cytotoxic agents as their active cytotoxic agent is a small molecule.

Illustrative of such second systemic antileukemia cytotoxic agents are liposomal daunorubicin, liposomal annamycin, sphingosomal vincristine, liposomal cytarabine, a calicheamicin-conjugated CD33 antibody called gemtuzumab ozogamicin and a chimer of CD30 antibody and monomethyl auristatin E called brentuximab vedotin.

Briefly, liposomes are generally spherically-shaped artificial vesicles typically prepared from cholesterol and phospholipid molecules that constitute one or two bilayers and encapsulate the small molecule second systemic cytotoxic agent to assist delivery. See, Akbarzadeh et al., *Nanoscale Res Lett*, 8:102 (2013).

Calicheamicin, is a high molecular weight small molecule (1368 Da), and contains four linked saccharides interrupted by a benzothioate S-ester linkage as well as an ene-diyne group that cleaves DNA sequences. Calicheamicin is too toxic to be used alone, $LD_{50}$ in nude mice of 320 µg/kg [DiJoseph et al., *Blood* 103:1807-1814 (2004)]. Similarly, monomethyl auristatin exhibits general (broad range), high toxicity [$IC_{50}$<1 nM for several cancer cell lines; ApexBio Technology Product Catalog (2013)] that is mediated by linkage to an antibody against CD30 (a TNF receptor-family member that is a cell membrane protein and cancer marker) was reported useful against large cell lymphoma and Hodgkin's disease [Francisco et al., *Blood* 102:1458-1465 (2003)], whereas linkage to an anti-CD79b monoclonal provided an advantage in treating three xenograft models of NHL [Dornan et al., *Blood* 114:2721-2729 (2009)].

A systemic anti-leukemia medication that is a small molecule (non-proteinaceous, less than about 1000 grams/mole) or a larger proteinaceous molecule, is administered to the subject mammal to be treated such that the medication spreads throughout the subject's body. Intravenous administration is one preferred method to achieve that spread of medication. On the other hand, imatinib is usually administered orally.

Illustrative small molecule anti-cancer medications useful for treating leukemia include doxorubicin, etoposide, vincristine, cisplatin, irinotecan and cytarabine were used in parental application Ser. No. 16/688,319, whereas an exemplary proteinaceous molecule is egasparaginase. Of those small molecule medications, doxorubicin, etoposide and vincristine each of which would be administered IV to a mammalian subject appeared to synergize in treatment with a sub-lethal dose of PV-10® aqueous RB disodium solution, and are preferred.

It is to be understood that administration of any of the second leukemia systemic cytotoxic agents discussed herein can be undertaken multiple times. Such multiple administrations are within the purview of the treating physician, and can be made in conjunction with an administration of the HX compound first leukemia cytotoxic agent or can be carried out separately.

A useful effective dosage of a small molecule systemic anti-leukemia medication is the dosage set out in the labeling information of a FDA-, national- or international agency-approved medication. Typically, monotherapy dose schedules are set by determining the maximum tolerated dose (MTD) in early-stage clinical trials. The MTD (or a close variation thereon) is then promulgated to later-stage clinical trials for assessment efficacy and more detailed assessment of safety. These MTDs frequently become the established therapeutic dose upon completion of clinical testing. However, because the small molecule, systemic anti-leukemia medication is contemplated for use with an HX compound in a solid or liquid formulation, a MTD is the maximal amount that would normally be used, and that amount is to be titrated downward following usual procedures.

Exemplary dosing schedules for several systemic anti-cancer (anti-leukemia) medications (agents) that can be combined with halogenated xanthene therapy in the present invention are provided in Table A, below. It is noted that several of the medications listed below are "small molecules" as defined above, whereas others are large, proteinaceous molecules such as antibodies, preferably monoclonal antibodies, inhibit inflammatory chemokine activity. They are nonetheless administered systemically. The medications of Table A are usually used as single active agents. However, one or more can also be used together, particularly the antibodies, as is the case with the immune checkpoint inhibitor antibodies that are discussed hereinafter.

TABLE A

Exemplary systemic immunomodulatory or targeted anticancer agents

| Systemic Agent | Typical Dose Schedule |
|---|---|
| adalimumab | 80 mg initial dose followed in 1 week by 40 mg every other week SQ |

TABLE A-continued

Exemplary systemic immunomodulatory
or targeted anticancer agents

| Systemic Agent | Typical Dose Schedule |
| --- | --- |
| brodalumab | 210 mg subcutaneously (SC) at Weeks 0, 1, and 2, then 210 mg SC q2wk |
| certolizumab pegol | 400 mg initially and at weeks 2 and 4 followed by 200 mg every other week or 400 mg Q4 weeks maintenance SQ |
| etanercept | 50 mg twice weekly for 3 months followed by 50 mg once weekly SQ |
| golimumab | 50 mg once a month SQ |
| guselkumab | 100 mg subcutaneous injection once every 8 weeks, after starter doses at weeks 0 and 4 |
| infliximab | 5 mg/kg given as an IV induction regimen at 0, 2, and 6 weeks followed by a maintenance regimen of 5 mg/kg every 8 weeks thereafter |
| ixekizumab | 160 mg initial dose followed Q2 weeks with 80 mg until week 12 then 80 mg Q4 weeks SQ |
| sarilumab | 200 mg every 2 weeks as a subcutaneous injection |
| secukinumab | 300 mg every week for 4 weeks then 300 mg every 4 weeks SQ |
| ustekinumab | Less than 100 kg: 45 mg initially, week 4 followed by 45 mg every 12 weeks SQ More than 100 kg: 90 mg initially, week 4 followed by 90 mg every 12 weeks SQ |
| apremilast | Titrated dose over 5 days to work up to 30 mg twice daily PO |
| methotrexate | Weekly single oral, IM or IV 10 to 25 mg per week or divided 2.5 mg dose at 12 hour intervals for three doses |
| cyclosporine | Initial dose 2.5 mg/kg/day taken twice daily as divided (BID); dose titrated up to 4 mg/kg/day BID if response and laboratory abnormalities don't ensue. |
| azathioprine | Used off label for skin diseases, 1.0 mg/kg oral or IV as a single dose or twice a day, dose maximum is 2.5 mg/kg/day. |

Because of additive or synergistic effects, the combination therapy and method of treatment of the present invention generally permit use of the systemic agent at a level at or below the typical dose schedule for the systemic agent, such as those described in Table A, when used with an IV administration therapy, such as that described below. However, the dosing schedules provided in Table A provide a useful guide for beginning treatment from which dosages can be titrated to lessened amounts as seen appropriate by the physician caring for a given patient.

It is noted that a HX compound and a second cytotoxic anti-leukemia agent need not be administered together nor by the same means of administration. Thus, a pill or capsule form can be used for can be used to administer the HX compound first cytotoxic anti-leukemia agent, whereas the small or large molecule second anti-leukemia agent is administered by IV or orally, like imatinib. Those skilled in the art are aware of the various methods of administering anti-leukemia agents.

A second type of second systemic cytotoxic agent useful for combination treatment with a halogenated xanthene such as that present in aqueous RB disodium solution or a before-described solid dosage form is an immune checkpoint inhibitor, that can also be viewed as a special systemic anti-leukemia medication. An immune checkpoint inhibitor is a drug that binds to and blocks certain checkpoint proteins made by immune system cells such as T cells and some leukemia cells. When not blocked, those proteins inhibit immune responses, helping keep immune responses in check and keeping T cells or other immune cells from killing leukemia cells. Blocking those immune checkpoint proteins releases the "brakes" on the immune system permitting immune cells to become activated and kill leukemia cells.

A useful immune checkpoint inhibitor is preferably a human or humanized monoclonal antibody or binding portion thereof whose administration blocks the action of those certain proteins. That blockage permits the immune system to recognize the leukemia cells as foreign and assist in eliminating those leukemia cells from the body.

Illustrative immune checkpoint inhibitors include the anti-CTLA-4 (cytotoxic T lymphocyte-associated antigen 4) monoclonal antibodies ipilimumab and tremelimumab that are designed to counter down-regulation of the immune system by blocking CTLA-4 activity and thus augment T cell response against leukemia. Similarly, monoclonal antibodies such as pidilizumab, nivolumab, tislelizumab, spartalizumab, cemiplimab, pembrolizumab, camrelizumab, sintilimab, toripalimab, and dostarlimab bind to PD-1 (programmed death 1) receptor to counter down-regulation of the immune system and augment T cell responses to cancerous cells. Three monoclonal antibodies that target the immune checkpoint protein ligand (anti-PD-L1) for the PD-1 receptor (anti-PD-1) are atezolizumab, avelumab, and durvalumab. Initial work with antibodies to the PD-1 receptor ligands, PD-L1 and PD-L2, such as BMS-936559 and MEDI4736 (durvalumab) to PD-L1, also indicate inhibition of down-regulation of the immune system and an augmented T cell response against leukemia.

The above immune checkpoint inhibitor antibodies have been found useful when administered singly along with a HX compound as well as using two different types of immune checkpoint inhibitors along with an HX compound. A poster by Patel et al., AMERICAN SOCIETY of CLINICAL ONCOLOGY (ASCO) 2020 VIRTUAL SCIENTIFIC PROGRAM May 29-31, 2020 provided data from a study that utilized rose bengal disodium that was injected intratumorally into uveal melanoma tumors metastatic to the liver along with either a systematic administration of anti-PD-1, or systemic administrations of both anti-PD-1 and CTLA-4 antibodies.

More recently, several further groups of antibodies with checkpoint inhibitor activity have been identified, and because of their similarity of action, are deemed herein to be immune checkpoint inhibitors. One illustrative group immunoreact with the cell surface receptor OX40 (CD134) to stimulate proliferation of memory and effector T-lymphocytes, and thereby stimulate a T-cell-mediated immune response against cancerous cells. Exemplary such humanized anti-OX40 monoclonal antibodies include those presently referred to in the literature as gsk3174998 (IgG1), pogalizumab (MOXR0916), MED10562 and the human anti-OX40 IgG2 antibody designated PF-04518600 (PF-8600).

Another group immunoreacts with lymphocyte activation gene 3 protein (anti-LAG-3; CD223) that negatively regulates T lymphocytes by binding to the extracellular domain of the ligand, thus avoiding autoimmunity caused by T cell overactivation. LAG-3 is an important immune checkpoint in vivo and plays a balanced regulatory role in the human immune system [Shan et al., Oncol Lett 20:207 (2020)].

The molecule LAG-3 blocks the signal transduction pathway of T cell activation; however, the intracellular segment of the LAG-3 molecule produces immunosuppressive signals, which have been found to regulate CD4+T cell activity. LAG-3 regulates the immune response of T cells in three ways: First, it directly inhibits the proliferation and activation of T cells via negative regulation of T cells. Second, it can promote the inhibitory function of regulatory T cells (Tregs), and the T cell response can then be indirectly inhibited. Third, it can prevent T cell activation by regulating the function of antigen presenting cells (APCs) [Joller et al., Curr Top Microbiol Immunol 410:127-156 (2017)].

To date, no monoclonal antibody to LAG-3 is known to be been approved for sale and use by the US Food and Drug Administration. Studies are ongoing using a humanized IgG4 monoclonal antibody from Merck referred to as MK-4280, and another from Bristol Myers Squibb with the INN name relatlimab.

A still further type of immune checkpoint inhibitor is a monoclonal antibody against CD47 and macrophage checkpoint inhibitor that interferes with recognition of CD47 by the SIRPα receptor on macrophages, thus blocking the "don't eat me" signal used by cancer cells to avoid being ingested by macrophages. This monoclonal, whose INN name is magrolimab, is being developed by Giliad Sciences, Inc. in several hematologic and solid tumor malignancies, including myelodysplastic syndrome (MDS). Magrolimab has been granted Fast Track Designation by the FDA for the treatment of myelodysplastic syndrome (MDS), acute myeloid leukemia (AML), diffuse large B-cell lymphoma (DLBCL) and follicular lymphoma. Magrolimab has also been granted Orphan Drug Designation by the FDA for MDS and AML and by the European Medicines Agency for AML.

Monoclonal antibodies to T cell immunoglobulin and mucin domain 3 (anti-TIM-3), another checkpoint marker, are in early development by Novartis Oncology Co. under the INN name sabatolimab (earlier MBG-453) for use in MDS and AML therapy based on differential leukemic stem cell expression, its role as a co-inhibitory T-cell co-receptor, and possibly a role in promoting antibody-dependent cellular phagocytosis (ADCP). TIM-3 is expressed on AML leukemic progenitors but is not seen on normal hematopoietic stem cells and its expression has been correlated with severity of myelodysplastic syndromes as well as the likelihood of progression to AML. There are currently multiple trials of TIM-3 antibody MBG-453 in frontline myelodysplastic syndromes and AML, with encouraging antileukemic activity presented when used in combination with decitabine.

Intact monoclonal antibodies, as well their paratope-containing portions (binding site-containing portions) such as Fab, Fab', F(ab')2 and Fv regions, as well as single-stranded peptide binding sequences can be useful as immune checkpoint protein inhibitors. Most of these antibodies are administered via an IV route. Intact checkpoint inhibiting monoclonal antibodies have half-lives in a human body of about one to three weeks [e.g., Yervoy® (ipilimumab) terminal $t_{1/2}$=15.4 days; package insert December 2013; Keytruda® (pembrolizumab) terminal $t_{1/2}$=23 days; package insert March 2017], and single-stranded oligo or polypeptides tend to have shorter half-lives in vivo.

Because of the relatively short half-lives of the small molecule second cytotoxic anti-leukemia agents and a halogenated xanthene compound-containing medicament, both medicaments can be administered in a single composition or in separate compositions. If administered separately, it is preferred to administer both types of anti-cancer (anti-leukemia) agent within minutes to about 3 hours of each other. More preferably, both are administered within less than one hour of the other.

The word "administration" is used herein to mean the beginning of a treatment regimen. Thus, swallowing a tablet or other per os dosage form is the beginning of a treatment regimen, as is the time at which an IV flow is begun. When both first and second cytotoxic anti-leukemia agents are present together in the same, single composition, administration begins when that unitary composition enters the subject's body.

Where the second cytotoxic systemic anti-leukemia agent is an immune checkpoint inhibitor such as a monoclonal antibody, the halogenated xanthene compound and the second cytotoxic anti-leukemia agent immune checkpoint inhibitor can be administered together or one before the other, with the second cytotoxic antileukemia agent immune checkpoint inhibitor being administered up to about one month prior to the halogenated xanthene. Preferably, the two cytotoxic anti-leukemia agents are administered together or with the second systemic cytotoxic anti-leukemia agent immune checkpoint inhibitor being administered within a few days after the halogenated xanthene. A second systemic cytotoxic anti-leukemia agent immune checkpoint inhibitor can also be administered about one month after the halogenated xanthene.

Studies

Mice:

Female C17 SCID mice from Charles River

Cell Line Used in Xenograft:

The SEM cell line was initially established from a 5 year old female with B acute lymphoblastic leukemia. It carries the MLL-AFFF1 gene fusion and heterozygous for CDKN2A and TP53. The utility of this cell line in anti-cancer drug sensitivity studies has been described (Barretina et al. Nature 483:603-607, 2012).

$2.5 \times 10^6$ exponentially growing SEM cells [labelled with green fluorescent protein (GFP)] were injected intravenously into each animal and the establishment of tumors was monitored. After 4 weeks to permit the growth of the tumors, mice were randomized to three groups.

Group 1 (n=9). Control:

These animals received 100 µL of PBS given orally twice a week for two weeks.

Group 2 (n=8). Treatment Cohort I:

These animals received 25 µL of PV-10® (10% rose bengal disodium w/v in 0.9 percent in aqueous saline) diluted in PBS to a final volume of 100 µL and given orally by gavage twice a week for 2 weeks.

Group 3 (n=8). Treatment Cohort II.

These animals received 12.5 µL of PV-10® (as discussed above) diluted in PBS to a final volume of 100 µL and given orally by gavage twice a week for 2 weeks.

Evidence of disease progression was monitored in all animals and survival was followed up to 120 days following the initiation of treatment. Data are presented in FIG. 1 as Kaplan-Meier estimates.

As is seen from the graphs of FIG. 1, oral delivery of the HX compound is clearly evidenced by dose-dependent survival of the treated mice.

The results disclosed in parental application Ser. No. 16/688,319 showed that eleven commercially available leukemia cell lines derived from patients with either primary or relapsed pediatric leukemia that were treated with PV-10® and two primary leukemia samples in cell culture could be killed by administration of increasing doses of PV-10®. Cell viability was measured by alamar blue assay, 96 hours post-treatment.

PV-10® administration decreased leukemia cell viability in a concentration and time dependent manner in the eleven pediatric leukemia cell lines (mean $IC_{50}$ 92.8 µM), and three primary leukemia samples (mean $IC_{50}$ 122.5 µM) examined. The results show that PV-10 is cytotoxic to leukemia cell lines with a mean $IC_{50}$ value of 92.8 µM (Table 1, below) and is cytotoxic to two primary leukemia samples with a mean $IC_{50}$ value of 122.5 µM (Table 2, below).

TABLE 1*

| Cell Line | Cell Type | PV-10 $IC_{50}$ µM |
|---|---|---|
| KOPN8 | Infant ALL | 150 |
| SUPB15 | B-ALL | 129 |
| CEM-C1 | T-ALL | 121 |
| TIB-202 | AML | 118 |
| SEM | B-ALL | 99 |
| CCRF-SB | B-ALL | 88 |
| Kasumi1 | AML | 72 |
| MV4-11 | Biphenotypic | 68 |
| Molm13 | AML | 42 |
| Molt4 | T-ALL | 41 |
| Molt3 | T-ALL | 35 |
| | Mean | 92.8 |

*Half maximal inhibitory concentration ($IC_{50}$) values for pediatric leukemia cell lines treated with PV-10® for 96 hours.

TABLE 2**

| Cell Type | PV-10 $IC_{50}$ µM |
|---|---|
| T-ALL | 150 |
| Infant AML | 95 |
| Mean | 122.5 |

**Half maximal inhibitory concentration ($IC_{50}$) values for primary pediatric leukemia samples treated with PV-10 ® for 96 hours.

Similar results were separately obtained using leukemia cell lines CCRF-CEM, HL-60(TB), K-562, MOLT-4, RPMI-8226 and SR.

It was surprising that leukemia cells could be killed at all at the concentrations of RB disodium used in these studies, which come out to approximately $10^{-4}$ to about $10^{-5}$ molar based on the $IC_{50}$ values. Even so, the concentrations of HX compound required were greater than those believed achieved by oral administration in the present studies as was discussed previously. Thus, it was still more surprising that 62.5% of the HX Compound-treated leukemic mice survived for 120 days whereas the untreated leukemic mice and those treated with lesser amounts of HX compound exhibited much poorer survival rates as are shown by the data in FIG. 1.

Each of the patents, patent applications and articles cited herein is incorporated by reference. The articles "a" and "an" are used herein to refer to one or to more than one (i.e., to at least one) of the grammatical object of the article. Each of the patents, patent applications and articles cited herein is incorporated by reference.

The foregoing description and the examples are intended as illustrative and are not to be taken as limiting. Still other variations within the spirit and scope of this invention are possible and will readily present themselves to those skilled in the art.

The invention claimed is:

1. A method of treating a mammalian subject having leukemic cells comprising the step of orally administering a therapeutically effective amount of a halogenated xanthene, a pharmaceutically acceptable salt, a lactone, or a Cl-$C_4$ alkyl or aromatic ester thereof (HX compound) as a first leukemia cytotoxic agent dissolved or dispersed in a pharmaceutically acceptable solid or liquid composition to said mammalian subject having leukemic cells, wherein said first cancer cytotoxic agent halogenated xanthene, pharmaceutically acceptable salt or $C_1$-$C_4$ alkyl ester thereof is rose bengal disodium salt.

2. The method according to claim 1, wherein said oral administration is repeated.

3. The method according to claim 1, wherein said composition is a solid.

4. The method according to claim 3, wherein the said HX compound is dissolved in or dispersed in or on a solid diluent medium.

5. The method according to claim 3, wherein the solid composition is in the form of a tablet, lozenge, or a plurality of generally spherical sugar prills.

6. The method according to claim 5, wherein said solid composition is comprised of generally spherical sugar prills coated with one or a plurality of layers of said HX compound.

7. The method according to claim 3, wherein said solid composition is coated with a barrier film that reduces the rate of dissolution and/or disintegration of the composition in aqueous media.

8. The method according to claim 7, wherein said barrier film coating is an enteric coating that dissolves and/or disintegrates at a physiological pH value of 5 or greater.

9. The method according to claim 1, wherein said composition is an aqueous liquid.

10. The method according to claim 9, wherein said aqueous liquid composition is as an osmolality that is less than that of normal human osmolality.

11. A method of treating a mammalian subject having leukemic cells comprising the steps of orally administering a therapeutically effective amount of a halogenated xanthene, a pharmaceutically acceptable salt, a lactone, or a Cl-$C_4$ alkyl or aromatic ester thereof (HX compound) as a first leukemia cytotoxic agent dissolved or dispersed in a pharmaceutically acceptable solid or liquid composition to said mammalian subject having leukemic cells, wherein said administration step is carried out in conjunction with a second administration to said mammalian subject of a second therapeutically effective amount of a second, differently-acting systemic leukemia cytotoxic agent dissolved or dispersed in a pharmaceutically acceptable medium, wherein said second, differently-acting systemic leukemia cytotoxic agent is a small molecule, a proteinaceous molecule that inhibits inflammatory chemokine activity, ionizing radiation therapy and intact checkpoint inhibitor antibodies or paratope-containing portions thereof, wherein said first cancer cytotoxic agent halogenated xanthene, pharmaceutically acceptable salt or $C_1$-$C_4$ alkyl ester thereof is rose bengal disodium salt.

12. The method according to claim 11, wherein said second leukemia cytotoxic agent is dissolved or dispersed in a pharmaceutically acceptable solid medium.

13. The method according to claim 12, wherein the pharmaceutically acceptable solid medium containing the second leukemia cytotoxic agent is administered per os.

14. The method according to claim 11, wherein second leukemia cytotoxic agent is ionizing radiation.

15. The method according to claim 11, wherein said small molecule exhibits synergy with said first leukemia cytotoxic agent.

16. The method according to claim 11, wherein said second leukemia cytotoxic agent is dissolved or dispersed in a pharmaceutically acceptable aqueous medium.

17. The method according to claim 16, wherein the pharmaceutically acceptable aqueous medium containing the second leukemia cytotoxic agent is administered intravenously.

18. The method according to claim 11, wherein second leukemia cytotoxic agent is a small molecule having a molecular weight of about 150 to about 1000 Da.

19. The method according to claim 18, wherein said small molecule is selected from one or more of the group consisting of vinblastine, vincristine, imatinib, monomethyl auristatin, etoposide, daunorubicin, doxorubicin, cladribine, fludarabine, mitoxantrone, 6-thioguanine, methotrexate, 6-mercaptopurine, azacytidine, annamycin, sorafenib, clofarabine, cisplatin, irinotecan and cytabarine.

20. The method according to claim 17, wherein the second leukemia cytotoxic agent comprises intact monoclonal antibodies or paratope-containing portions thereof.

21. The method according to claim 20, wherein said intact monoclonal antibodies or paratope-containing portions thereof are immune checkpoint inhibitors.

22. The method according to claim 21, wherein said immune checkpoint inhibitors bind to one or more proteinaceous materials selected from one or more of the group consisting of anti-CTLA-4, anti-PD-1, anti-PD-L1, anti-PD-L2, anti-OX40, anti-LAG-3, anti-CD47 and anti-TIM-3.

23. The method according to claim 20, wherein said intact monoclonal antibodies are proteinaceous molecules that inhibit inflammatory chemokine activity that are selected from the group consisting of adalimumab, brodalumab, certolizumab pegol, etanercept, golimumab, guselkumab, infliximab, ixekizumab, sarilumab, secukinumab, and ustekinumab.

24. The method according to claim 17, wherein said antibodies or paratope-containing portions thereof are administered after administration of said HX compound.

25. The method according to claim 17, wherein said antibodies or paratope-containing portions thereof are administered before administration of said HX compound.

26. The method according to claim 17, wherein said antibodies or paratope-containing portions thereof are administered concurrently with administration of said HX compound.

27. The method according to claim 17, wherein said first HX compound and said second leukemia cytotoxic agents are administered simultaneously to within about 3 hours of each other.

* * * * *